US006861550B2

(12) United States Patent
Honma et al.

(10) Patent No.: US 6,861,550 B2
(45) Date of Patent: Mar. 1, 2005

(54) POLYHYDROXYALKANOATE CONTAINING 3-HYDROXYBENZOYLALKANOIC ACID AS MONOMER UNIT, AND METHOD FOR PRODUCING THE SAME

(75) Inventors: Tsutomu Honma, Atsugi (JP); Etsuko Sugawa, Atsugi (JP); Tetsuya Yano, Atsugi (JP); Shin Kobayashi, Kawasaki (JP); Takeshi Imamura, Chigasaki (JP); Takashi Kenmoku, Fujisawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 699 days.

(21) Appl. No.: 09/791,610

(22) Filed: Feb. 26, 2001

(65) Prior Publication Data

US 2003/0100084 A1 May 29, 2003

(30) Foreign Application Priority Data

| Feb. 29, 2000 | (JP) | 2000-054668 |
|---|---|---|
| Feb. 29, 2000 | (JP) | 2000-054669 |
| Sep. 27, 2000 | (JP) | 2000-294634 |

(51) Int. Cl.$^7$ .............................................. C07C 69/73
(52) U.S. Cl. ........................................................ 560/53
(58) Field of Search ............................................ 560/53

(56) References Cited

U.S. PATENT DOCUMENTS

| 4,393,167 A | 7/1983 | Holmes et al. ................ 525/64 |
| 4,477,654 A | 10/1984 | Holmes et al. .............. 528/361 |
| 4,876,331 A | 10/1989 | Doi ............................. 528/361 |
| 5,292,860 A | 3/1994 | Shiotani et al. .............. 528/361 |
| 5,334,698 A | 8/1994 | Witholt et al. .............. 528/354 |
| 2002/0022253 A1 | 2/2002 | Honma |

FOREIGN PATENT DOCUMENTS

| EP | 0288908 | 11/1988 |
| EP | 0392687 | 10/1990 |
| EP | 1 188 782 | 3/2002 |
| EP | 1 201 763 | 5/2002 |
| JP | 5-93049 | 4/1993 |
| JP | 6-15604 | 3/1994 |
| JP | 7-14352 | 2/1995 |
| JP | 7-265065 | 10/1995 |
| JP | 8-19227 | 2/1996 |
| JP | 2642937 | 5/1997 |
| JP | 9-191893 | 7/1997 |
| JP | 2989175 | 10/1999 |

OTHER PUBLICATIONS

Derwent WPI, See. Ch, Acc. No. 1993–137938 for JP 5–074492.
Reháková, et al.; "Depolymerization Reactions of Hyaluronic Acid In Solution;" Int. J. Biol. Macromol. 16, 3, 1994) 121–124.
Lytl , t al.; "Filtration Siz s of Human Immunod ficiency Virus Typ 1 and Surrogat Virus s Us d To T st Barri r Mat rials;" Appl. and Envirn. Microb., 58 2, (1992) 747–749.
Kim, et al.; "Preparation nad Characterization of Poly(β–hydroxyalkanoates) Obtain d from *Pseudomonas olevorans* Grown with Mixtures of 5–Phenylvaleric Acid and n–Alkanoic Acids"; Macromolecules 24 (1991) 5256–5260.
Curley, et al.; "Production of Poly(3–hydroxyalkanoates) Containing Aromatic Substituents by *Pseudomonas oleovorans*"; Macromolecules 29, (1996) 1762–1766.
Kim, et al; "Poly–3–hydroxyalkanoates Produced from *Pseudomonas olevorans* Grown with ω—Phenoxyalkanoates"; Macromolecules 29, (1996) 3432–3435.
Andújar, et al.; "Polyesters Produced by *Pseudomonas oleovorans* Containing Cycloh xyl Groups"; Macromolecules 30, (1997) 1611–1615.
Aróstegul, et al.; "Bacterial Polyesters Produced by *Pseudomonas oleovorans* Containing Nitrophenyl Groups"; Macromolecules 32, (1999) 2889–2895.
Fritzsche, et al.; "An Unusual Bacterial Polyester With A Phenyl Pendant Group"; Makromol Chem. 191 (1990) 1957–1965.
Ritt r, t al.; "Poly(3–hydroxy–5–ph noxyp ntanoate–co–3–hydroxy–9–ph noxy–nonanoate) from *Pseudomonas oleovorans*"; Macromol. Ch m. Phys. 195 (1994) 1665–1672.
Kim et al., Bioengineering of poly(β–hydroxyalkanoates) for . . . substituents; Can. J. Microbiol., 41 (Suppl. 1), 32–43 (1995).
Antoun, et al., "Production of a Chiral Polyester by *Pseudomonas oleovorans* Grown With 5–Phenyl–2,4–Pentadienoic Acid", Chirality, vol. 3, pp. 492–494 (1991).
Biodegradable Plastic Handbook, pp. 178–197 (1995).

*Primary Examiner*—Paul J. Killos
(74) *Attorney, Agent, or Firm*—Fitzpatrick, Cella, Harper & Scinto

(57) ABSTRACT

Microorganisms capable of producing novel polyalkanoates having 3-hydroxybenzoylalkanoic acids as monomer units by utilizing benzoylalkanoic acids as starting materials are cultured in media containing benzoylalkanoic acids and saccharides, and the polyhydroxyalkanoates produced in the culture cells are extracted and recovered.

24 Claims, 6 Drawing Sheets

SEQUENCE LISTING

<160> NUMBER OF SEQ ID NOS: 1

<210> SEQ ID NO 1
<211> LENGTH: 1501
<212> TYPE: DNA
<213> ORGANISM: Pseudomonas jessenii 161 strain.

<400> SEQUENCE: 1

```
tgaacgctgg cggcaggcct aacacatgca agtcgagcgg atgacgggag cttgctcctg      60
aattcagcgg cggacgggtg agtaatgcct aggaatctgc ctggtagtgg gggacaacgt     120
ctcgaaaggg acgctaatac cgcatacgtc ctacgggaga aagcagggga ccttcgggcc     180
ttgcgctatc agatgagcct aggtcggatt agctagttgg tgaggtaatg gctcaccaag     240
gcgacgatcc gtaactggtc tgagaggatg atcagtcaca ctggaactga gacacggtcc     300
agactcctac gggaggcagc agtggggaat attggacaat gggcgaaagc ctgatccagc     360
catgccgcgt gtgtgaagaa ggtcttcgga ttgtaaagca ctttaagttg ggaggaaggg     420
cattaaccta atacgttagt gttttgacgt taccgacaga ataagcaccg gctaactctg     480
tgccagcagc cgcggtaata cagagggtgc aagcgttaat cggaattact gggcgtaaag     540
cgcgcgtagg tggtttgtta agttggatgt gaaagccccg ggctcaacct gggaactgca     600
ttcaaaactg acaagctaga gtatggtaga gggtggtgga atttcctgtg tagcggtgaa     660
atgcgtagat ataggaagga acaccagtgg cgaaggcgac cacctggact gatactgaca     720
ctgaggtgcg aaagcgtggg gagcaaacag gattagatac cctggtagtc cacgccgtaa     780
acgatgtcaa ctagccgttg ggagccttga gctcttagtg gcgcagctaa cgcattaagt     840
tgaccgcctg gggagtacgg ccgcaaggtt aaaactcaaa tgaattgacg ggggcccgca     900
```

```
caagcggtgg agcatgtggt ttaattcgaa gcaacgcgaa gaaccttacc aggccttgac    960
atccaatgaa ctttccagag atggatgggt gccttcggga acattgagac aggtgctgca   1020
tggctgtcgt cagctcgtgt cgtgagatgt tgggttaagt cccgtaacga gcgcaaccct   1080
tgtccttagt taccagcacg taatggtggg cactctaagg agactgccgg tgacaaaccg   1140
gaggaaggtg gggatgacgt caagtcatca tggcccttac ggcctgggct acacacgtgc   1200
tacaatggtc ggtacagagg gttgccaagc cgcgaggtgg agctaatccc acaaaaccga   1260
tcgtagtccg gatcgcagtc tgcaactcga ctgcgtgaag tcggaatcgc tagtaatcgc   1320
gaatcagaat gtcgcggtga atacgttccc gggccttgta cacaccgccc gtcacaccat   1380
gggagtgggt tgcaccagaa gtagctagtc taaccttcgg gaggacggtt accacggtgt   1440
gattcatgac tggggtgaag tcgtaccaag gtagccgtag gggaacctgc ggctggatca   1500
c                                                                  1501
```

POLYHYDROXYALKANOATE CONTAINING 3-HYDROXYBENZOYLALKANOIC ACID AS MONOMER UNIT, AND METHOD FOR PRODUCING THE SAME

BACKGROUND OF THE INVENTION

1. Field of the Invention

The present invention relates to a novel polyhydroxyalkanoate (hereinafter, sometimes abbreviated to "PHA"). Further, the present invention relates to a method for high efficient production of PHA using microorganisms having an ability of producing PHA and accumulating it in their cells.

2. Related Background Art

Heretofore, a variety of microorganisms have been reported to produce and accumulate poly-3-hydroxybutyric acid (hereinafter, sometimes abbreviated to "PHB") or other PHAs in the cells ("Biodegradable Plastics Handbook", edited by Biodegradable Plastics Society, issued by NTS Co., Ltd., P178–197). These polymers can be used for production of different kinds of products with melting processes etc. like the conventional plastics. Further, since these polymers have the advantage of being completely decomposed by microorganisms in nature because of their biodegradability, they would not remain in the natural environment to cause pollution unlike many conventional synthetic polymer compounds. Furthermore, they are also excellent in biological compatibility and expected to be applied to medical soft members and the like.

It is known that such microbial PHAs may have a variety of compositions and structures depending on types of the microorganisms, the compositions of culture media, culture conditions, etc. used for their production, and up to now, studies regarding the control of these compositions and structures have been carried out from the point of view of improving the properties of PHAs.

For example, it has been reported that *Alcaligenes eutropus* strain H16 (ATCC No. 17699) and its mutant strains produce copolymers of 3-hydroxybutyric acid (hereinafter, sometimes abbreviated to "3HB") and 3-hydroxyvaleric acid (hereinafter, sometimes abbreviated to "3HV") at a variety of composition ratios by verying the carbon sources in their culture (Japanese Patent Publication Nos. 6-15604, 7-14352, 8-19227 and the like).

Japanese Patent Application Laid-Open No. 5-74492 discloses a method in which the copolymer of 3HB and 3HV is produced by bringing *Methylobacterium* sp., *Paracoccus* sp., *Alcaligenes* sp. or *Pseudomonas* sp. into contact with primary alcohol having 3 to 7 carbons.

Japanese Patent Application Laid-Open Nos. 5-93049 and 7-265065 disclose that two-component copolymers of 3HB and 3-hydroxyhexanoic acid (hereinafter, sometimes abbreviated to "3HHx") are produced by culturing *Aeromonas caviae* using oleic acid or olive oil as a carbon source.

Japanese Patent Application Laid-Open No. 9-191893 discloses that *Comamonas acidovorans* IFO 13852 produces polyester having 3HB and 4-hydroxybutyric acid as monomer units in culture with gluconic acid and 1,4-butanediol as a carbon source.

Also, in recent years, intensive researches about PHA composed of 3-hydroxyalkanoate (hereinafter, sometimes abbreviated to "3HA") of medium-chain-length (abbreviated to "mcl") having up to about 12 carbons have been performed. Synthetic routes of such PHAs can be classified broadly into two types, and their specific examples will be shown in (1) and (2) below.

(1) Synthesis Using β-oxidation

Japanese Patent No. 2642937 discloses that PHA having monomer units of 3-hydroxyalkanoate having 6 to 12 carbons is produced by giving a noncyclic aliphatic hydrocarbon as a carbon source to *Pseudomonas oleovorans* ATCC 29347.

Furthermore, it has been reported in Appl. Environ. Microbiol, 58 (2), 746 (1992) that *Pseudomonas resinovorans* produces polyester having 3-hydroxybutyric acid, 3-hydroxyhexanoic acid, 3-hydroxyoctanoic acid and 3-hydroxydecanoic acid (in a quantitative ratio of 1:15:75:9) as monomer units, using octanoic acid as a sole carbon source, and also produces polyester having 3-hydroxybutyric acid, 3-hydroxyhexanoic acid, 3-hydroxyoctanoic acid and 3-hydroxydecanoic acid (in a quantitative ratio of 8:62:23:7) as units, using hexanoic acid as a sole carbon source. Herein, it is assumed that 3HA monomer units having a chain length longer than that of fatty acids as a starting material are made by way of a fatty acid synthetic route that will be described in (2).

(2) Synthesis Using Fatty Acid Synthetic Route

It has been reported in Int. J. Biol. Macromol., 16 (3), 119 (1994) that *Pseudomonas* sp. strain 61-3 produces polyester composed of 3-hydroxyalkanoic acids such as 3-hydroxybutyric acid, 3-hydroxyhexanoic acid, 3-hydroxyoctanoic acid, 3-hydroxydecanoic acid and 3-hydroxydodecanoic acid; and 3-hydroxyalkenoic acids such as 3-hydroxy-5-cis-decenoic acid and 3-hydroxy-5-cis-dodecenoic acid as units, using sodium gluconate as a sole carbon source.

By the way, the biosynthesis of PHA is usually carried out by a PHA synthase using "D-3-hydroxyacyl-CoA", which is formed as an intermediate of a variety of metabolic pathways in the cell, as a substrate.

Herein, "CoA" means a "coenzyme A". As described in the prior art of the above (1), the biosynthesis of PHA is carried out using "D-3-hydroxyacyl-CoA" formed in the "β-oxidation cycle" as a starting substance in the case where fatty acids such as octanoic acid and nonanoic acid are used as carbon sources.

Reactions through which PHA is biosynthesized by way of the "β-oxidation cycle" will be shown below.

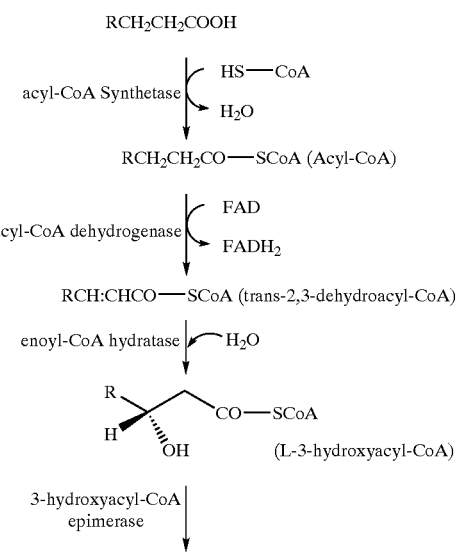

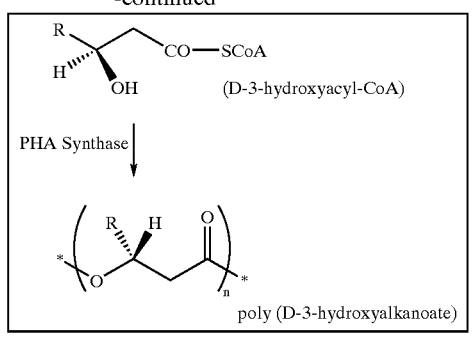

poly (D-3-hydroxyalkanoate)

On the other hand, as described in the prior art of the above (2), in the case where the PHA is biosynthesized using saccharides such as glucose, it is carried out using "D-3-hydroxyacyl-CoA", which is converted from "D-3-hydroxyacyl-ACP" formed in the "fatty acid synthesis pathway", as a starting substance.

Herein, "ACP" means an "acyl carrier protein".

By the way, as described previously, any PHA synthesized in both (1) and (2) described above is PHA composed of monomer units having alkyl groups in side chains, that is, "usual PHA". However, if a wider range of application of the microbial PHA like this, for example an application as a functional polymer is considered, it is expected that PHAs having substituents (e.g., phenyl groups) other than alkyl groups introduced in the side chains are significantly useful. Such other substituents include an unsaturated hydrocarbon, ester group, allyl group, cyano group, halogenated hydrocarbon, epoxide or the like.

With respect to the synthesis of PHA having such substituent (that is, other than alkyl groups) introduced in the side chain (hereinafter, referred to as "unusual PHA" if necessary), the synthesis using β-oxidation has been reported, for example, a report regarding PHA having an aryl group and the like introduced in the side chain can be found in Macromolecules, 24, p5256–5260 (1991). Specifically, it has been reported that *Pseudomonas oleovorans* produces PHA comprising 3HV, 3-hydroxyheptanoic acid, 3-hydroxynonanoic acid, 3-hydroxyundecanoic acid and 3-hydroxy-5-phenylvaleric acid (hereinafter, sometimes abbreviated to "3HPV") in a quantitative ratio of 0.6:16.0:41.1:1.7:40.6 as monomer units in the amount of 160 mg per liter (L) of culture solution (ratio in dry weight to the cell mass is 31.6%), using 5-phenylvaleric acid (hereinafter, sometimes abbreviated to "PVA") and nonanoic acid (mole ratio of 2:1, total concentration of 10 mmol/L) as substrates, and also produces PHA comprising 3HHx, 3-hydroxyoctanoic acid, 3-hydroxydecanoic acid and 3HPV in a quantitative ratio of 7.3:64.5:3.9:24.3 as monomer units in the amount of 200 mg per L of culture solution (ratio in dry weight to the cell mass is 39.2%), using PVA and octanoic acid (mole ratio of 1:1, total concentration of 10 mmol/L) as substrates. It is assumed that the PHA in this report is synthesized through mainly the β-oxidation pathway because nonanoic acid and octanoic acid are used.

The related description is also found in Macromol. Chem., 191, 1957–1965 (1990) and Chirality, 3, 492–494 (1991) where changes of polymer properties presumably caused by containing 3HPV are recognized.

As described above in microbial PHAs, different compositions and structures can be obtained by changing types of microorganisms, the compositions of culture medium, culture conditions and the like which are used for their production, however, when considering their application to plastics, their properties can not be said to be satisfactory yet. In order to further expand the usable range of microbial PHAs, it is important to investigate wider improvement of the properties, and therefore it is essential to develop and search PHAs comprising monomer units having a variety of structures, production methods therefor, and microorganisms capable of efficiently producing the desired PHAs.

On the other hand, as described previously, the PHA (unusual PHA) having substituents introduced in the side chain can be also expected to be developed as a "functional polymer" provided with significantly useful functions and characteristics owing to characteristics etc. of the introduced substituents by selecting substituents to be introduced corresponding to the desired characteristics, therefore it is an important problem to develop and search superior PHAs having both such functionality and biodegradability compatible with each other, production methods therefor, and microorganisms capable of efficiently producing the desired PHAs.

Other examples of PHAs having such substituents introduced in the side chain include PHAs having the above described phenyl group and further phenoxy group in the side chain.

For another examples of the phenyl group, it has been reported in Macromolecules, 29, 1762–1766 (1996) that *Pseudomonas oleovorans* produces PHA comprising 3-hydroxy-5-(4-tolyl)valeric acid as monomer units by culturing in the culture medium containing 5-(4-tolyl)valeric acid (5-(4-methylphenyl)valeric acid) as a substrates.

Further, it has been reported in Macromolecules, 32, 2889–2895 (1999) that *Pseudomonas oleovorans* produces PHA comprising 3-hydroxy-5-(2,4-dinitrophenyl)valeric acid and 3-hydroxy-5-(4-nitrophenyl)valeric acid as monomer units by culturing in the culture medium containing 5-(2,4-dinitrophenyl)valeric acid and nonanoic acid as substrates.

In addition, for an example of the phenoxy group, it has been reported in Macromol. Chem. Phys., 195, 1665–1672 (1994) that *Pseudomonas oleovorans* produces PHA comprising 3-hydroxy-5-phenoxyvaleric acid and 3-hydroxy-9-phenoxynonanic acid as units from 11-phenoxyundecanoic acid.

Further, it has been reported in Macromolecules, 29, 3432–3435 (1996) that *Pseudomonas oleovorans* is used to produce PHAs comprising 3-hydroxy-4-phenoxybutyric acid and 3-hydroxy-6-phenoxyhexanoic acid as units from 6-phenoxyhexanoic acid; PHAs comprising 3-hydroxy-4-phenoxybutyric acid, 3-hydroxy-6-phenoxyhexanoic acid and 3-hydroxy-8-phenoxyoctanoic acid as units from 8-phenoxyoctanoic acid; and PHAs comprising 3-hydroxy-5-phenoxybutyric acid and 3-hydroxy-7-phenoxyheptanoic acid as units from 11-phenoxyundecanoic acid, respectively. The yields of polymers cited from this report are as follows.

TABLE 1

| Carbon Source (alkanoate) | Weight of Dry Cell (mg/L) | Weight of Dry Polymer (mg/L) | Yield (%) |
|---|---|---|---|
| 6-Phenoxyhexanoic acid | 950 | 100 | 10.5 |
| 8-Phenoxyoctanoic acid | 820 | 90 | 11 |
| 11-Phenoxyundecanoic acid | 150 | 15 | 10 |

Furthermore, in Can. J. Microbiol., 41, 32–43 (1995), PHA is successfully produced which comprises 3-hydroxy-p-cyanophenoxyhexanoic acid or 3-hydroxy-p-nitrophenoxyhexanoic acid as monomer units, using octanoic acid and p-cyanophenoxyhexanoic acid or p-nitrophenoxyhexanoic acid as substrates and using *Pseudomonas oleovorans* strain ATCC29347 and *Pseudomonas putida* strain KT2442.

In Japanese Patent No. 2989175, homopolymers composed of a 3-hydroxy-5-(monofluorophenoxy)pentanoate (3H5(MFP)P) unit or 3-hydroxy-5-(difluorophenoxy) pentanoate (3H5(DFP)P) unit, and copolymers comprising at least the 3H5(MFP)P unit or 3H5(DFP)P unit; *Pseudomonas putida* for synthesizing these polymers; and methods of producing the aforementioned polymers using the genus *Pseudomonas*.

These productions are carried out in the following "two-step culture".

Culture Time: 24 Hours for First Step; 96 Hours for Second Step

Substrates for each step and polymers obtained are shown below.

(1) Polymer obtained: 3H5(MFP)P homopolymer
   Substrate for first step: citric acid, yeast extract
   Substrate for second step: monofluorophenoxyundecanoic acid
(2) Polymer obtained: 3H5(DFP)P homopolymer
   Substrate for first step: citric acid, yeast extract
   Substrate for second step: difluorophenoxyundecanoic acid
(3) Polymer obtained: 3H5(MFP)P copolymer
   Substrate for first step: octanoic acid or nonanoic acid, yeast extract
   Substrate for second step: monofluorophenoxyundecanoic acid
(4) Polymer obtained: 3H5(DFP)P copolymer
   Substrate for first step: octanoic acid or nonanoic acid, yeast extract
   Substrate for second step: difluorophenoxyundecanoic acid As the effect, it is described that polymers having phenoxy groups substituted with one to two fluorine atoms in the terminal side chain can be synthesized by assimilating medium-chain fatty acids having substituents, and that stereoregularity and water-repellency can be added to them, while maintaining a high melting point and good workability.

In addition, PHAs containing a cyclohexyl group in monomer units are expected to show polymer properties different from those of PHAs containing usual aliphatic hydroxyalkanoic acids as units, and an example of their production by *Pseudomonas oleovorans* has been reported (Macromolecules, 30, 1611–1615 (1997)).

According to this report, when culturing *Pseudomonas oleovorans* in the medium where nonanoic acid (hereinafter, abbreviated to "NA") coexists with cyclohexylbutyric acid (hereinafter, abbreviated to "CHBA") or cyclohexylvaleric acid (hereinafter, abbreviated to "CHVA"), the PHAs containing units of the cyclohexyl group and units derived from the nonanoic acid are obtained (each ratio is unknown).

For the yield etc., it has been reported that the quantitative ratios of CHBA and NA were changed in the condition of 20 mmol/L of the total substrate concentration with respect to CHBA to obtain the results as shown in Table 2.

TABLE 2

| NA:CHBA | CDW | PDW | Yield | Unit |
|---|---|---|---|---|
| 5:5 | 756.0 | 89.1 | 11.8 | NA, CHBA |
| 1:9 | 132.8 | 19.3 | 14.5 | NA, CHBA |

CDW: Cell (Dry Weight) (mg/L)
PDW: Polymer (Dry Weight) (mg/L)
Yield: PDW/CDW (%)

However, the polymer yield per culture solution is insufficient in this case, and aliphatic hydroxyalkanoic acids derived from nonanoic acid are also mixed in the monomer units of the PHA itself obtained.

Thus, when producing PHAs with various substituents introduced in the side chain using microorganisms, as seen in the aforementioned report examples of *Pseudomonas oleovorans*, a method is used in which alkanoates having substituents to be introduced are used as carbon sources for growth, in addition to being used as polymer ingredients.

However, the method in which alkanoates having substituents to be introduced are used as carbon sources for growth, in addition to being used as polymer ingredients are expected to supply an energy source based on generation of acetyl-CoA by way of the β-oxidation from the above-described alkanoates. In such methods, the acetyl-CoA can not be generated by the β-oxidation unless the substrate has a chain-length to a certain extent, therefore it is a significant problem that alkanoates usable as substrates of PHAs are limited.

Further generally, substrates each having a chain-length shortened by two-methylene chains each through the β-oxidation are newly formed and are incorporated as monomer units of PHAs, therefore the synthesized PHAs often become copolymers comprising monomer units each having a different chain length by two-methylene chains. In the report described above, the copolymers are produced which are composed of 3 types of monomer units: 3-hydroxy-8-phenoxyoctanoic acid derived from 8-phenoxyoctanoic acid as a substrate, 3-hydroxy-6-phenoxyhexanoic acid and 3-hydroxy-4-phenoxybutyric acid which are byproducts derived from the metabolites.

When intending to obtain PHA composed of a single monomer unit, it is extremely difficult to use this method from this point of view. Further, in the method provided that supply of an energy source is based on the generation of acetyl-CoA by β-oxidation, it is a significant problem that growth of microorganisms is slow and syntheses of PHAs take long time and that the yield of synthesized PHAs is likely to lower.

Therefore, in addition to alkanoates having substituents intended to be introduced, generally the method is used which is presumably effective in extracting PHAs after culturing microorganisms in the medium coexisting with medium-chain-fatty acids such as octanoic acid and nonanoic acid as carbon sources for growth.

However, according to the present inventors' consideration, the PHAs synthesized through the β-oxidation pathway where medium-chain-fatty acids such as octanoic acid and nonanoic acid as described above are used as carbon sources for growth have the low purity, and 50% of polymers obtained or more is mcl-3HA monomer units, that are, "usual PHA" units, which are monomer units (e.g., 3-hydroxyoctanoic acid, 3-hydroxynonanoic acid, etc.) derived from carbon sources for growth. These mcl-3HA units are adhesive polymers in single composition at an ordinary temperature, and when mcl-3HA units are mixed in large amounts with the objective PHAs of the present invention, they significantly lower the glass transition temperature (Tg) of the polymers.

Thus, when obtaining a hard polymer property at an ordinary temperature, a mixture of the mcl-3HA monomer units is undesirable. It is known also that such a heterogeneous side chain structure interferes with the interaction derived from intramolecular or intermolecular side chain structures so that it significantly affects crystallinity or orientation. When attaining improvement of the polymer property and addition of functionality, a mixture of the mcl-3HA monomer units is significantly problematic.

A solution of the problem is to have a purification step for separating/removing "unobjective" monomer units such as mcl-3HA monomer units derived from a carbon source for growth in order to obtain PHAs composed of only a monomer unit having a specified substituent. However, there are problems that it complicates the operation and can not avoid significant reduction of the yield.

There is also a significant problem that it is extremely difficult to remove only unobjective monomers when forming copolymers from the objective and unobjective monomer units. Particularly, when aiming at the syntheses of PHAs containing monomer units having a side chain such as a group obtained from an unsaturated hydrocarbon, ester group, allyl group, cyano group, nitro group or a group obtained from a halogenated hydrocarbon, a group introduced with epoxide or the like as the side chain structure, the mcl-3HA monomer units often form a copolymer with the objective monomer unit so that it is extremely difficult to remove the mcl-3HA monomer units after synthesis of the PHAs.

SUMMARY OF THE INVENTION

Therefore, the present inventors have attained the recognition that development of a biosynthetic method for obtaining "unusual PHAs" in high purity is essential, in the case of considering application to functional polymers. Thus, it was presumably highly useful and important to develop excellent polymers provided with both functionality and biodegradability as described above, microorganisms capable of producing the present polymers and accumulating them in the cells, and a method for efficiently biosynthesizing the present polymers in high purity.

The present invention solves the above-described problems; and provides PHAs (unusual PHAs) comprising monomer units of various structures having substituents in the side chains useful as device materials, medical materials and the like; and provides a method for producing the present "unusual PHAs" using microorganisms, particularly a production method in which the mixture of unobjective monomer units is reduced and an objective "unusual PHA" can be obtained with a high purity and a high yield.

Accordingly, while the present inventors aim at development of PHAs having substituents in the side chain which are useful as device materials, medical materials and the like, they have searched microorganisms capable of producing different types of PHAs and accumulating them in the cells, and assiduously repeated studies on a method for producing the desired PHAs using such microorganisms.

As a result, the present inventors found that microorganisms capable of producing novel PHAs comprising 3-hydroxybenzoylalkanoic acid represented by the following Chemical Formula [2] as a monomer unit and accumulating them in the cells, further that the PHAs can be biosynthesized by culturing these microorganisms under coexisting of benzoylalkanoic acids represented by the following Chemical Formula [10] with saccharides, and that the PHAs obtained thereby had a relatively high purity.

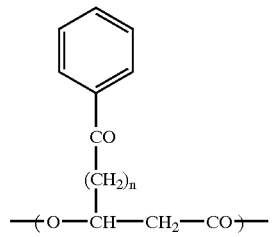

[2]

wherein n is any integer of 1 to 8.

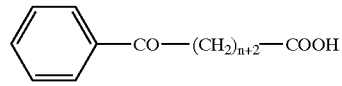

[10]

wherein n is any integer of 1 to 8. More specifically, the present inventors found microorganisms capable of using as a starting material, 4-benzoylbutyric acid (hereinafter, sometimes abbreviated to "BzBA") represented by the Chemical Formula [12]:

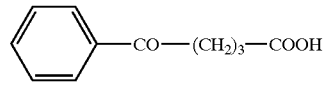

[12]

5-benzoylvaleric acid (hereinafter, sometimes abbreviated to "BzVA") represented by the Chemical Formula [13]:

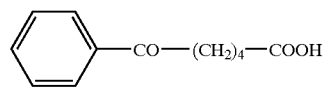

[13]

6-benzoylhexanoic acid (hereinafter, sometimes abbreviated to "BzHxA") represented by the Chemical Formula [14]:

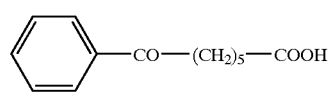

[14]

7-benzoylheptanoic acid (hereinafter, sometimes abbreviated to "BzHpA") represented by the Chemical Formula [15]:

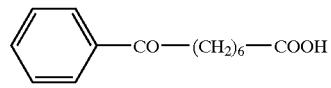

[15]

and 8-benzoyloctanoic acid (hereinafter, sometimes abbreviated to "BzOA") represented by the Chemical Formula [16]:

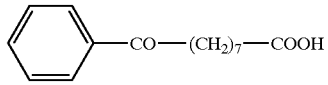

[16]

and capable of producing and accumulating in the cells the novel PHAS containing as monomer units, 3-hydroxy-4-benzoylbutyric acid (hereinafter, sometimes abbreviated to "3HBzB") represented by the Chemical Formula [5]:

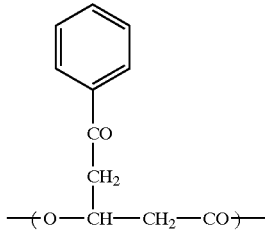

[5]

3-hydroxy-5-benzoylvaleric acid (hereinafter, sometimes abbreviated to 3HBzV) represented by the Chemical Formula [6]:

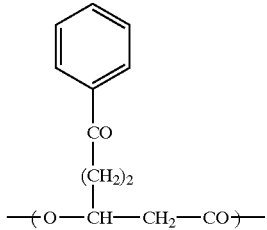

[6]

3-hydroxy-6-benzoylhexanoic acid (hereinafter, sometimes abbreviated to "3HBzHx") represented by the Chemical Formula [7]:

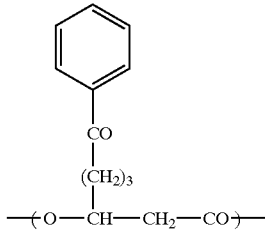

[7]

and 3-hydroxy-7-benzoylheptanoic acid (hereinafter, sometimes abbreviated to "3HBzHp") represented by the Chemical Formula [8]:

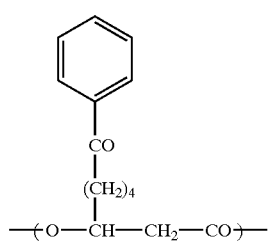

[8]

3-hydroxy-8-benzoyloctanoic acid (hereinafter, sometimes abbreviated to "3HBzO") represented by the Chemical Formula [9]:

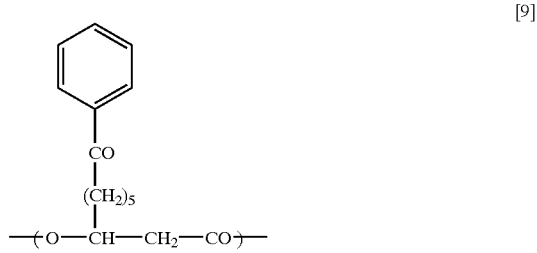

[9]

respectively. Further, it was found that the present PHAs can be biosynthesized by culturing these microorganisms under coexisting of BzBA, BzVA, BzHxA, BzHpA or BzOA with saccharides and that the present PHAs obtained had relatively high purity, thereby leading to complete the present invention.

In other words, the present invention relates to polyhydroxyalkanoates having a composition of monomer units represented by the following Formula [1]:

$A_xB_{(1-x)}$

[1]

wherein A is at least one or more monomer units represented by the following Chemical Formula [2], B is at least or more selected from monomer units represented by the following Chemical Formula [3] or [4], and x is not less than 0.01 to less than 1.

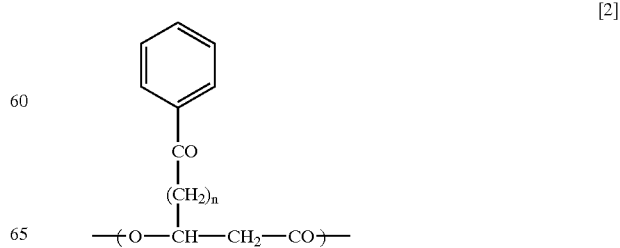

[2]

wherein n is any integer of 1 to 8.

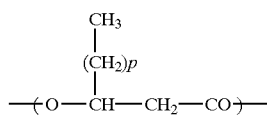

[3]

wherein p is any integer of 0 to 10.

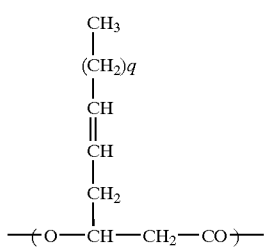

[4]

wherein q is 3 or 5.

In addition, the present invention relates to a method for producing polyalkanoates, comprising the step of culturing microorganisms in the medium containing benzoylalkanoic acids represented by the Chemical Formula [10]:

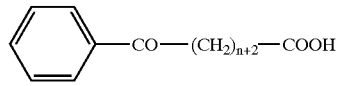

[10]

wherein n is any integer of 1 to 8, and producing, by the microorganisms, the polyalkanoates having the corresponding monomer units represented by the Chemical Formula [11]:

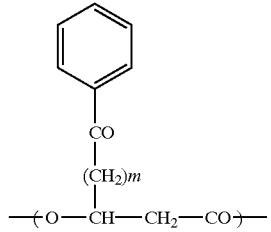

[11]

wherein m is at least one or more selected from the group consisting of n, n−2, n−4 and n−6, and is an integer not smaller than 1.

Herein, according to the present methods, saccharide compounds, for example, glucose, fructose, mannose and the like are used as substrates for growth of microorganisms so that monomer units derived from saccharides such as glucose are not contained at all or contained little in PHAs produced. From such a viewpoint, the present method differs fundamentally from the conventional methods for producing microbial PHAs using saccharides such as glucose.

According to the present invention, it is preferable to further have a step of isolating the PHAs produced by microorganisms.

According to the present invention, novel polyhydroxyalkanoates comprising 3-hydroxybenzoylalkanoic acids as monomer units and a method for producing the polyhydroxyalkanoates using microoraganisms are provided. The polyhydroxyalkanoates useful as functional polymers can be efficiently produced whereby they can be expected to be applicable to each field such as device materials and medical materials.

DETAILED DESCRIPTION OF THE PREFERRED EMBODIMENTS

Figure 1:
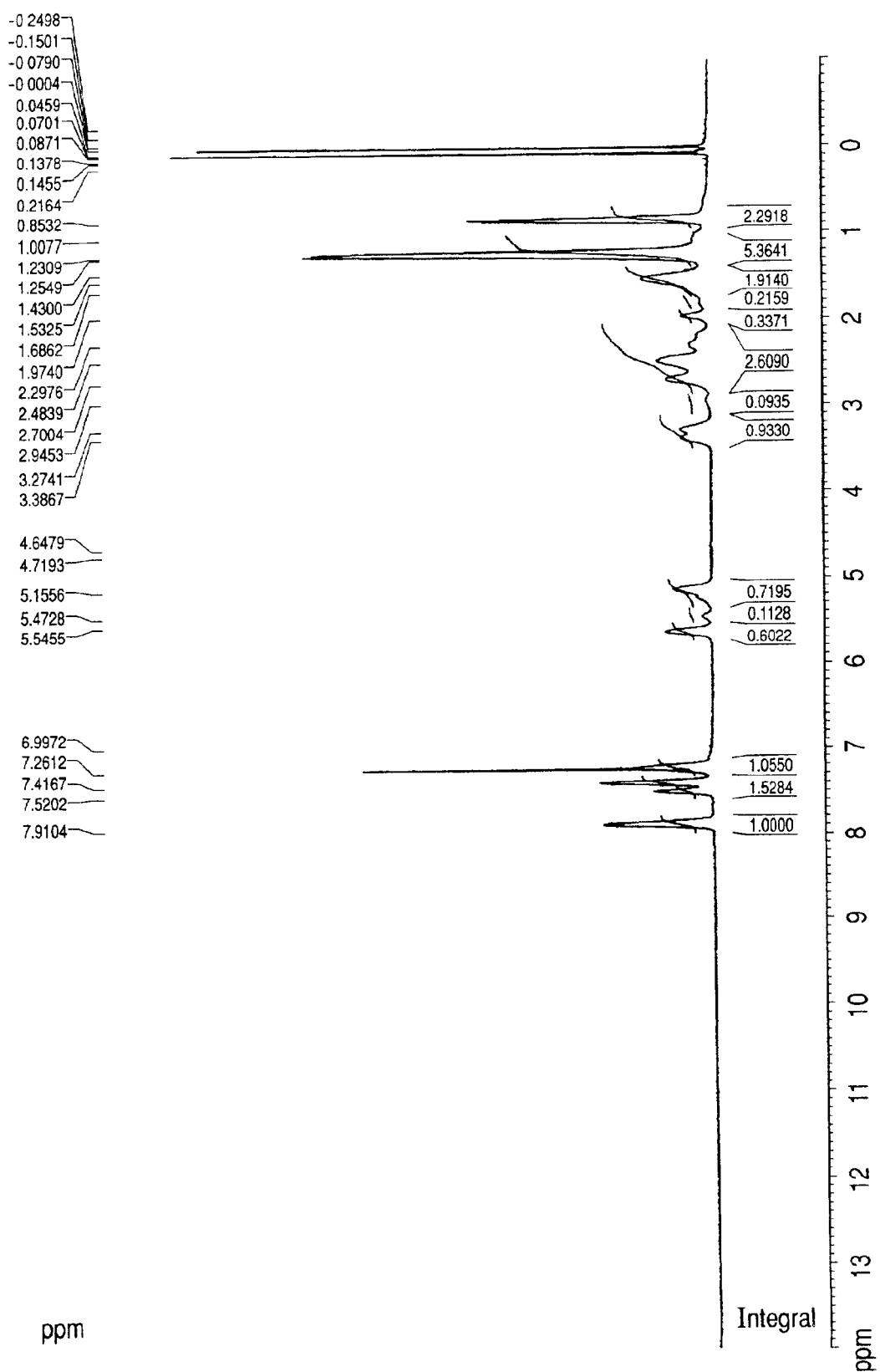
FIG. 1 is a graphical representation showing the $^1$H-NMR spectrum of a polymer using BzBA as a starting material in Example 1.

PHAs of the present invention are isotactic polymers generally composed of only the R-form.
<Organic Acids Associated with Saccharides and the TCA Cycle: Difference from Conventional Arts>

One of the methods for producing PHAs according to the present invention is characterized in that the contents of the objective monomer units are extremely increased or only the objective monomer units are obtained in the PHAs produced and accumulated by the microorganisms by adding only saccharides or organic acids associated with the TCA cycle as carbon sources other than the alkanoates, in addition to alkanoates for introduction of the desired monomer units, into the medium when culturing microorganisms. This accelerating effect of prioritizing the specified monomer units is obtained by adding only saccharides or organic acids associated with the TCA cycle as carbon sources other than the alkanoates into the medium.

In other words, the inventors have completed the present invention by obtaining the findings that the objective PHAs are obtained in much superior yields and purity, compared with the conventional methods using mcl-alkanoates such as nonanoic acid and octanoic acid as coexisting substrates, when culturing saccharides or organic acids associated with the TCA cycle as coexisting substrates together with alkanoates for introduction of the desired monomer units, and that such effect is obtained by the culturing method capable of generating acetyl-CoA, which is a carbon source and an energy source of microorganisms, by the method not depending on the β-oxidation.

According to the present invention, saccharide compounds, for example, glucose, fructose, mannose and the like are used as substrates for growth of microorganisms so that PHAs produced are composed of alkanoates for introduction of the desired monomer units coexisting with saccharides and the monomer units derived from the saccharides such as glucose are not contained at all or contained extremely little in them. From such a viewpoint, the present methods differ fundamentally in both the constitution and effect from the conventional methods for producing microbial PHAs using saccharides themselves such as glucose as starting substrates for introducing monomer units into PHAs.

The PHAs, production method and microorganisms of the present invention will be described in details below.

<Supplying System of PHA Monomer Units>

First, the "fatty acid synthesis pathway", which is one of systems supplying mcl-3HA monomer units being mixed into the objective PHAs will be described in details.

In the case where saccharides such as glucose are substrates, alkanoates necessary for cellular components are biosynthesized through the "fatty acid synthesis pathway" in which acetyl-CoA produced from saccharides through the "glycolytic pathway" is a starting substance. The fatty acid synthesis includes the de novo synthetic pathway and the carbon-chain elongation pathway, which will be described below.

1) De Novo Synthetic Pathway

This pathway is catalyzed by two enzymes which are acetyl-CoA carboxylase (EC 6.4.1.2) and fatty acid synthase (EC 2.3.1.85). The acetyl-CoA carboxylase is an enzyme interposing biotin, ultimately catalyzing the following reaction to produce malonyl-CoA from acetyl-CoA. The reaction is represented by the following Scheme [17].

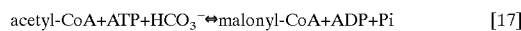

[17]

The fatty acid synthase is an enzyme catalyzing the reaction cycle of transfer-condensation-reduction-dehydration-reduction. The entire reactions are represented by the following Reaction Scheme [18].

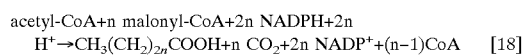

[18]

Herein, the reaction products may be free acids, CoA-derivatives or ACP-derivatives, depending on the type of enzymes.

Herein, the acetyl-CoA and malonyl-CoA are represented by the following Chemical Formulas [19] and [20].

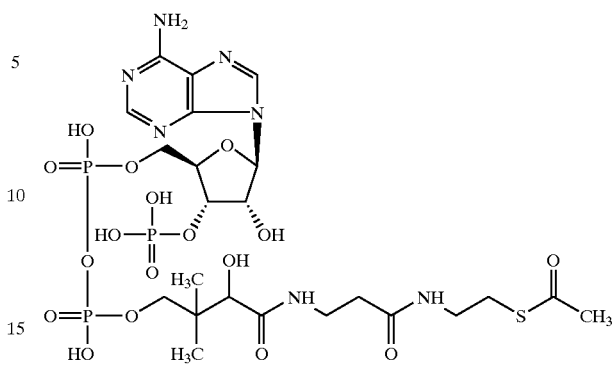

[19]

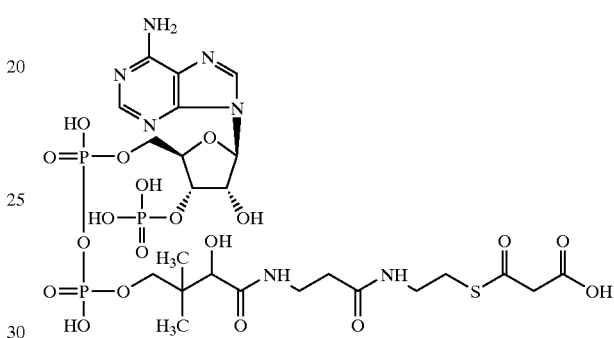

[20]

In addition, CoA is abbreviation of co-enzyme A represented by the following Chemical Formula [21].

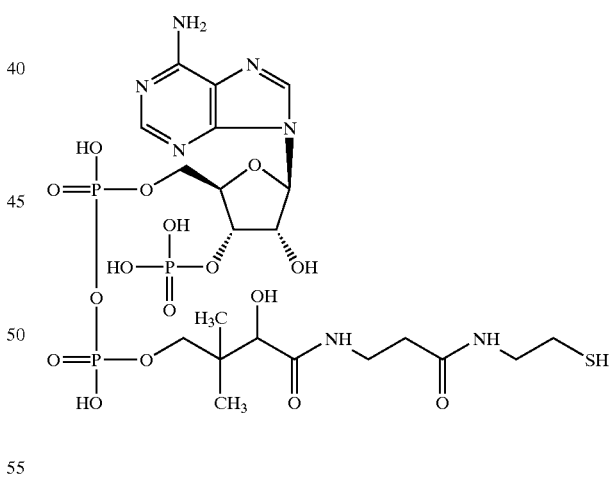

[21]

In this reaction pathway, "D-3-hydroxyacyl-ACP" which is to be the monomer substrate for the PHA biosynthesis is supplied as an intermediate through the route described below. Additionally, routes as shown in the following reaction schemes are extended finally to palmitic acid with repeated addition of two carbons. Therefore, as the monomer substrate for the PHA biosynthesis are provided seven "D-3-hydroxyacyl-ACPs" having even numbers of carbons, from "D-3-hydroxybutyryl-ACP" to "D-3-hydroxypalmityl-ACP".

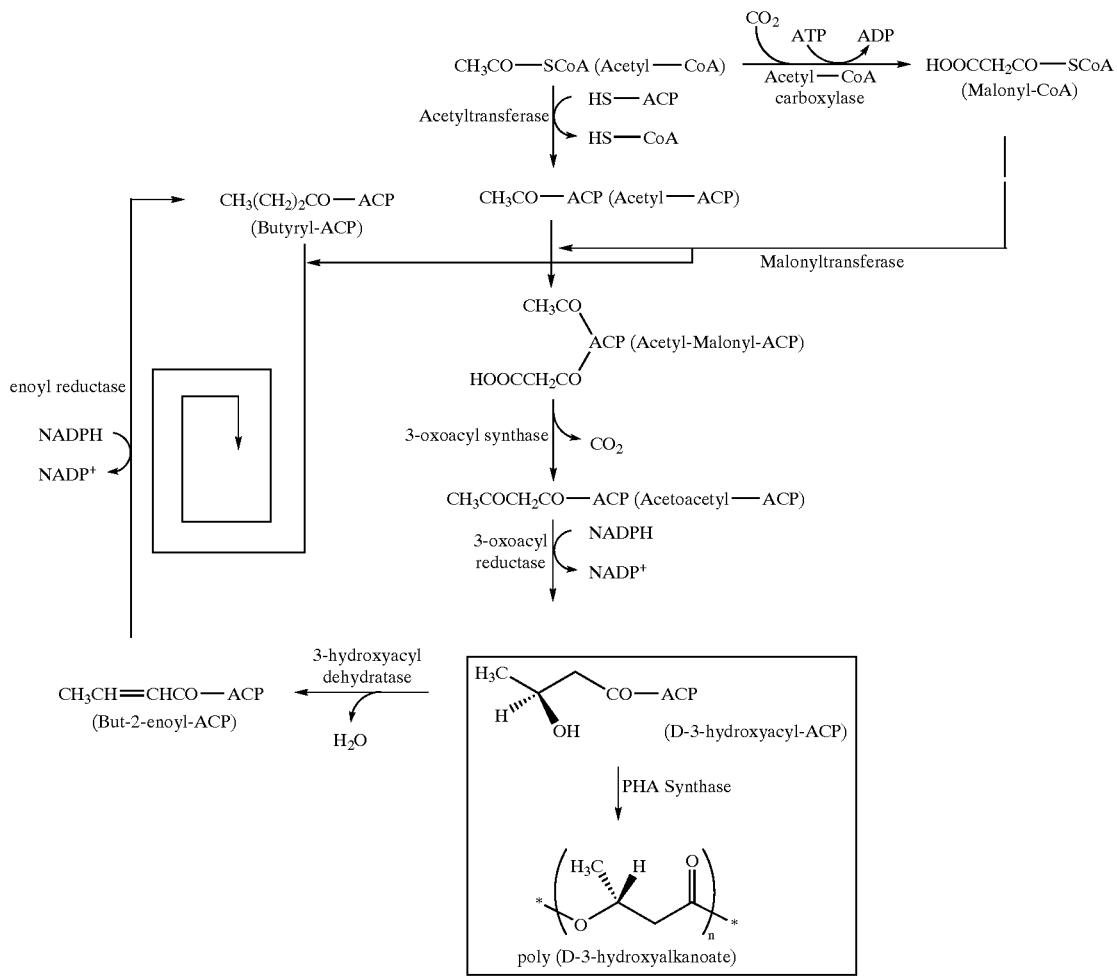

2) Carbon-Chain Elongation Pathway

This pathway is broadly divided into two pathways: in one of which, malonyl-ACP is added to acyl-ACP to ultimately convert them into acyl-ACP having the carbon chain extended with two carbons (and $CO_2$) (referred to as "Pathway A"), and in another, acetyl-CoA is added to acyl-CoA to ultimately convert them into acyl-CoA having the carbon chain extended with two carbons (referred to as "Pathway B"). Each pathway will be described below.

Pathway A

R—CO-ACP+malonyl-ACP→R—CO—CH$_2$—CO-ACP+CO2
R—CO—CH$_2$—CCO-ACP→R—CHOH—CH$_2$—CO-ACP→R—CH=CH—CO-ACP→R—CH$_2$—CH$_2$—CO-ACP Pathway B R—CO-CoA+acetyl-CoA→R—CO—CH$_2$—CO-CoA
R—CO—CH$_2$—CO-CoA→R—CHOH—CH$_2$—CO-CoA→R—CH=CH—CO-CoA→R—CH$_2$—CH$_2$—CO-CoA In both Pathways A and B, it is thought that "D-3-hydroxyacyl-CoA" or "D-3-hydroxyacyl-ACP" is yielded as an intermediate, and "D-3-hydroxyacyl-CoA" is utilized as the monomer substrate for the PHA synthesis as it is, while "D-3-hydroxyacyl-ACP" is utilized as the monomer substrate for the PHA synthesis after being converted to "D-3-hydroxyacyl-CoA" by ACP-COA transferase.

In the case where saccharides such as glucose and the like are used as a substrate, it is thought that an mcl-3HA monomer unit is formed via the "glycolytic pathway" and the "fatty acid synthesis pathway" within the microbial cells, as described above. In the case where organic acids involved in the TCA cycle are used as a substrate, acetyl-CoA is yielded directly from pyruvic acid by pyruvate dehydrogenase. Organic acids on the TCA cycle, for example, malic acid yields pyruvic acid by malate dehydrogenase, further, acetyl-CoA is yielded from the above-described reaction. Oxaloacetic acid yields phosphoenolpyruvic acid by phosphoenolpyruvate kinase, phosphoenolpyruvic acid yields pyruvic acid catalyzed by pyruvate kinase, further acetyl-CoA is generated from the above-described reaction. It is considered that Acetyl-CoA generated by these reactions yields the mcl-3HA monomer unit via the "fatty acid synthesis pathway".

It is considered that mcl-alkanoates, e.g. octanoic acid or nonanoic acid, or alkanoates which are added with a functional group other than the straight-chained aliphatic alkyl group at the terminal, e.g., 5-phenylvaleric acid, 5-(4-fluorophenyl)valeric acid, 6-phenylhaxanoic acid, 4-phenoxybutyric acid or 4-cyclohexylbutyric acid are converted to CoA derivatives by CoA ligase (EC 6.2.1.3, etc.), and converted to "D-3-hydroxyacyl-CoA" which becomes directly a monomer substrate of the PHA biosynthesis by the enzyme group functioning in the β-oxidation system.

In other words, it means that the mcl-3HA monomer unit formed from saccharides or organic acids associated with the TCA cycle is formed through extremely multistage-enzymatic reaction (i.e. indirectly), while the mcl-3HA monomer units are formed very directly from the mcl-alkanoates.

Herein, generation of acetyl-CoA carrying out growth of microorganisms will be described. In a method of coexisting with the mcl-alkanoates in addition to alkanoates for introduction of the objective monomer units, acetyl-CoA is generated through the β-oxidation system of these alkanoates. Comparing with alkanoates having a bulky substituent (alkanoates having substituents such as a phenyl group, phenoxy group or cyclohexyl group), generally the mcl-alkanoates is presumably excellent in the substrate affinity with the enzyme group of the β-oxidation system, so that acetyl-CoA is effectively generated by coexistence with the mcl-alkanoates. Therefore, it is advantageous for growth of microorganisms to use acetyl-CoA as both an energy source and a carbon source.

However, since the mcl-alkanoates via the β-oxidation system are converted directly into monomer units of PHAs, it is a significant problem that a large amount of the mcl-3HA monomer units are mixed in addition to the objective monomer units.

In order to solve this problem, it is desirable to select the substrates other than the mcl-alkanoates capable of effectively supplying acetyl-CoA or an energy source and a carbon source, and to use the method of coexisting with the objective alkanoates. As described previously, although acetyl-CoA can be converted into monomer units of PHAs through the fatty acid synthesis pathway, it is necessary to pass through more multistage reactions as compared to the mcl-alkanoates, and it is indirectly yielded. By suitably selecting culture conditions such as concentration of substrates capable of generating acetyl-CoA, it is possible to carry out the production method in which the mcl-3HAs are not substantially mixed or mixed little.

The production method to be widely used comprises the first step of culturing only growth of microorganisms, and the second step of adding only the objective alkanoate as a carbon source into the medium. Herein, since acyl-CoA ligase which is a starting enzyme for converting the present alkanoate into acyl-CoA needs ATP, according to the inventors' study, the results that the production method of coexisting with substrates usable for microorganisms as an energy source also at the second step was more effective were obtained, thereby leading to complete the present invention.

Microorganisms, culture steps and the like utilized in the present invention will be described below.
(Microorganisms)

For microorganisms used in the present invention, if BzBA, BzVA, BzHxA, BzHpA or BzOA can be used as a starting material to produce the corresponding PHAs comprising the above-described 3HBzB, 3HBzV, 3HBzHx, 3HBzHp or 3HBzO as a monomer unit, respectively, any microorganisms may be used. Further, within the scope attainable for the purposes of the present invention, plural microorganisms may be mixed and used if necessary.

The present inventors performed screening of microorganisms capable of producing the corresponding PHA comprising the above-described 3HBzB, 3HBzV, 3HBzHx, 3HBzHp or 3HBzO as a monomer unit by using BzBA, BzVA, BzHxA, BzHpA or BzOA as a substrate, respectively, and accumulating them in the cells. As a result, the present inventors have found that microorganisms isolated from soil which have producibility of PHAs and the desired ability are *Pseudomonas cichorii* strain H45, *Pseudomonas cichorii* strain YN2, *Pseudomonas jessenii* strain P161 and the like. Herein, strain H45 as deposition No. "FERM BP-7374", strain YN2 as deposition No. "FERM BP-7375" and strain P161 as deposition No. "FERM BP-7376" have been deposited each in Deposition Center of Patent Microorganisms, Research Institute of Biotechnology and Industry, the Agency of Industrial Science of Technology, the Ministry of Economy and Industry whose address is 1-3, Higashi 1-chome, Tsukuba-shi, Ibaraki-ken, 305 Japan, and are the microorganisms described in Japanese Patent Application No. 11-371863. In addition, the international deposition for these microorganisms has been carried out according to the Budapest Treaty. The international requisition and deposition Nos. for these microorganisms are as follows, strain H45: "FERM BP-7374" deposited Jun. 3, 1999, strain YN2: "FERM BP-7375" deposited Jun. 3, 1999 and strain P161: "FERM BP-7376" deposited Jul. 1, 1999.

The bacteriological properties of the above-described strains H45, YN2 and P161 will be enumerated as follows. For strain P161, the basic sequence of 16SrRNA will be shown in sequence No. 1.

<Bacteriological Properties of Strain H45>
(1) Morphological Properties
  Shape and size of cells: rod, 0.8 μm×1.0 to 1.2 μm
  Polymorphism of cells: negative
  Mobility: motile
  Sporulation: negative
  Gram staining: negative
  Colony shape: circular; entire, smooth margin; low convex, smooth surface; glossy; cream-colored
(2) Physiological Properties
  Catalase: positive
  Oxidase: positive
  O/F test: oxidative
  Nitrate reduction: negative
  Indole production: negative
  Acid production from glucose: negative
  Arginine dihydrolase: negative
  Urease: negative
  Esculin hydrolysis: negative
  Gelatin hydrolysis: negative
  β-Galactosidase: negative
  Fluorescent pigment production on King's B agar: positive
  Growth under 4% NaCl: negative
  Poly-β-hydroxybutyrate accumulation: negative
(3) Substrate Assimilation
  Glucose: positive
  L-Arabinose: negative
  D-Mannose: positive
  D-Mannitol: positive
  N-Acetyl-D-glucosamine: positive
  Maltose: negative
  Potassium gluconate: positive
  n-Capric acid: positive
  Adipic acid: negative
  dl-Malic acid: positive
  Sodium citrate: positive
  Phenyl acetate: positive <Bacteriological Properties of Strain YN2>
(1) Morphological Properties
  Shape and size of cells: rod, 0.8 μm×1.5 to 2.0 μm
  Polymorphism of cells: negative
  Mobility: motile
  Sporulation: negative
  Gram staining: negative
  Colony shape: circular; entire, smooth margin; low convex, smooth surface; glossy; translucent
(2) Physiological Properties
  Catalase: positive
  Oxidase: positive
  O/F test: oxidative
  Nitrate reduction: negative
  Indole production: positive
  Acid production from glucose: negative
  Arginine dihydrolase: negative
  Urease: negative
  Esculin hydrolysis: negative
  Gelatin hydrolysis: negative
  β-Galactosidase: negative
  Fluorescent pigment production on King's B agar: positive
  Growth under 4% NaCl: positive (weak growth)
  Poly-β-hydroxybutyrate accumulation: negative
  Tween 80 hydrolysis: positive
(3) Substrate Assimilation
  Glucose: positive
  L-Arabinose: positive
  D-Mannose: negative
  D-Mannitol: negative
  N-Acetyl-D-glucosamine: negative
  Maltose: negative
  Potassium gluconate: positive
  n-Capric acid: positive
  Adipic acid: negative
  dl-Malic acid: positive
  Sodium citrate: positive
  Phenyl acetate: positive
<Bacteriological Properties of Strain P161>
(1) Morphological Properties
  Shape and size of cells: sphere, φ0.6 μm rod, 0.8 μm×1.5 to 2.0 μm
  Polymorphism of cells: positive (extended type)
  Mobility: motile
  Sporulation: negative
  Gram staining: negative
  Colony shape: circular; entire, smooth margin; low convex, smooth surface; glossy; pale yellow
(2) Physiological Properties
  Catalase: positive
  Oxidase: positive
  O/F test: oxidative
  Nitrate reduction: positive
  Indole production: negative
  Acid production from glucose: negative
  Arginine dihydrolase: positive
  Urease: negative
  Esculin hydrolysis: negative
  Gelatin hydrolysis: negative
  β-Galactosidase: negative
  Fluorescent pigment production on King's B agar: positive
(3) Substrate Assimilation
  Glucose: positive
  L-Arabinose: positive
  D-Mannose: positive
  D-Mannitol: positive
  N-Acetyl-D-glucosamine: positive
  Maltose: negative
  Potassium gluconate: positive
  n-Capric acid: positive
  Adipic acid: negative
  dl-Malic acid: positive
  Sodium citrate: positive
  Phenyl acetate: positive
(Culture Step)
<General Culture>

The objective PHAs can be produced by culturing these microorganisms in the medium containing alkanoates for introduction of the desired monomer units and substrates for growth according to the present invention. Such PHAs are generally composed of only the R-form and are isotactic polymers.

In usual culture of microorganisms used for the production methods of PHAs according to the present invention, for example, preparation of stock cell strains, the cell count necessary for production of PHAs and growth for holding the active state and the like, the media containing requisite components for growth of microorganisms to be used are suitably selected and used. For example, any kinds of media such as general natural media (nutrient broth, yeast extract, etc.) and synthetic media added with nutrients may be used as long as they do not have a bad influence on growth and survival of microorganisms.

Any of culture methods using the culture such as the liquid culture, solid culture and the like can be used as long as the microorganisms can grow and produce the PHAs. Further, it may use any types: batch culture, fed batch culture, semicontinuous culture, continuous culture and the like. As forms of the liquid batch culture, methods for supplying oxygen include the shaking one using a shaking flask and the spinner aeration one using a jar fermenter. The multistage method in which these processes are connected to plural steps may be also adopted.

In the case where PHAs comprising 3HBzB, 3HBzV, 3HBzHx, 3HBzHp or 3HBzO as a monomer unit are produced using the above-described microorganisms, the inorganic media and the like may be used which contain at least the corresponding BzBA, BzVA, BzHxA, BzHpA or BzOA as a starting material for the PHA production, respectively, and carbon sources for growth of microorganisms. For the carbon sources for growth, nutrients such as yeast extract, polypeptone and meat extract can be used, further, they includes: saccharides, for example, aldoses such as glyceraldehyde, erythrulose, arabinose, xylose, glucose, galactose, mannose and fluctose, alditols such as glycerol, erythritol and xylitol, aldonic acids such as gluconic acid, uronic acids such as glucuronic acid and galacturonic acid, disaccharides such as maltose, sucrose and lactose, further organic acids or their salts such as pyruvic acid, malic acid, citric acid and succinic acid which are formed as intermediates in the TCA cycle, amino acids or their salts such as glutamic acid and the like, and if the compounds can yield acetyl-CoA without passing through the β-oxidation cycle, any of them can be used and suitably selected as substrates useful for cell strains to be used. Also, if the combination has little mixture of mcl-3HA, it is possible to select and use plural compounds. Among them, it is preferable to use particularly saccharides, more preferably at least one selected from the group consisting of glucose, fluctose and mannose. As a method of producing and accumulating PHAs by microorganisms, there is a method in which once they are grown sufficiently, then the cells are transferred to the medium in which a nitrogen source such as ammonium chloride is limited, the compounds to become substrates of the desired units are added to the medium and the cells are further cultured in this condition, whereby the producibility is improved in some cases. Specifically, it includes adoption of the multistage method in which the above-described processes are connected to plural steps. For example, there is a culture method in which after being cultured up to the point of steady state from the latter term of logarithmic growth in the inorganic media and the like containing about 0.05% to 5.0% of D-glucose and about 0.01% to 1.0% of BzBa, BzVA, BzHxA, BzHpA or BzOA, the cells are recovered with centrifugal separation and the like, and they are, further, cultured in the inorganic media containing about 0.01% to 1.0% of BzBA, BzVA, BzHxA, BzHpA or BzOA where nitrogen sources are limited to or substantially not present.

As the inorganic media to be used for the above-described culture method, any of them may be used provided that they contains the components such as phosphorus sources (e.g., phosphate, etc.) and nitrogen sources (e.g., ammonium salts, nitrate, etc.) by which microorganisms can grow, the inorganic salt media can include, for example, the MSB medium, E medium (J. Biol. Chem., 218, 97–106 (1956)), M9 medium or the like.

Herein, composition of the M9 medium used in Examples of the present invention is as follows.

$Na_2HPO_4$: 6.2 g
$KH_2PO_4$: 3.0 g
NaCl: 0.5 g
$NH_4Cl$: 1.0 g
(in 1 liter medium, pH 7.0)

For the better growth and production of PHAs, about 0.3% (v/v) solution of minor components, as shown below, preferably is added to the above-described inorganic salt medium.

[Minor Component Solution]

Nitrilotriacetic acid: 1.5; $MgSO_4$: 3.0; $MnSO_4$: 0.5; NaCl: 1.0; $FeSO_4$: 0.1; $CaCl_2$: 0.1; $COCl_2$; $ZnSO_4$: 0.1; $CuSO_4$: 0.1; $AlK(SO_4)_2$: 0.1; $H_3BO_3$: 0.1; $Na_2MoO_4$: 0.1; $NiCl_2$: 0.1
(in 1 liter)

For the culture temperature, it may be a temperature enabling good growth of the above-described cell strains, for example, 14 to 40° C., preferably about 20 to 35° C. are appropriate.

As a specific example, after being cultured in the inorganic media and the like containing about 0.05% to 5.0% of D-glucose and about 0.01% to 1.0% of BzBA, BzVA, BzHxA, BzHpA or BzOA followed by recovering the cells at the point from the latter term of logarithmic growth to the steady state, the desired PHAs can be extracted in which the unobjective monomer units are less mixed or are not present at all. Such PHAs are generally composed of only the R-form and are isotactic polymers.

The same amount of yeast extract in place of D-glucose may be given. In addition, it may use polypeptone, organic acids (e.g. lactic acid, pyruvic acid, citric acid, succinic acid, fumaric acid, malic acid, etc. and their salts) associated with the TCA cycle and their combination.

<Recovery of PHAs>

For obtaining PHAs from the culture solutions according to the present invention, the methods to be usually conducted can be applied. In the case where the PHAs are discharged in the culture solution, the methods for extraction from the culture solution and for their purification are used, and in the case where they are accumulated in the cells, the methods for extraction from the cells and their purification are used. For example, the most simple method for recovery of PHAs from the cultured cells of microorganisms is carried out by extraction with organic solvents such as chloroform which is usually conducted, while acetone other than chloroform is used sometimes. Also in the circumstance unlikely to use organic solvents, a method can be used in which PHAs are recovered after removing the cell components other than PHAs by treating with surfactants such as SDS, enzymes such as lysozyme and chemical agents such as EDTA, sodium hypochiorite, ammonia and the like. The PHAs have a number-average molecular weight of 10,000 to 1,000,000.

Culturing the microorganisms of the present invention, producing PHAs by the microorganisms of the present invention and accumulating them in the cells and recovering PHAs from the cells according to the present invention are not limited to the above described methods.

Examples will be shown below. Herein, the following "%" is based on the weight unless otherwise marked.

EXAMPLE 1

*Pseudomonas cichorii* strain YN2 was inoculated into 200 mL of the M 9 medium containing 0.5% D-glucose and 0.1% BzBA followed by being cultured with shaking at 30° C. at 125 strokes/min. After 48 hr, the cells were recovered by centrifugal separation, then resuspended into 200 ml of the M 9 medium containing 0.5% D-glucose and 0.1% BzBA without containing a nitrogen source ($NH_4Cl$), followed by being cultured with shaking at 30° C. at 125 strokes/min. After 42 hr, the cells were recovered by centrifugal separation, cleaned once with cold methanol and lyophilized.

This lyophilized pellet was suspended into 20 mL chloroform and stirred at 60° C. for 20 hr, and PHA was extracted. After filtrating the extracted solution through a membrane filter with the pore size of 0.45 μm, it was concentrated with a rotary evaporator, and the concentrated solution was reprecipitated in cold methanol, further only the precipitate was recovered followed by vacuum drying to obtain PHA.

After performing methanolysis of the obtained PHA according to the conventional method, it was analyzed using a gas chromatography-mass spectrometer (GC-MS, Shimadzu QP-5050, EI method) to identify the methyl ester compound of PHA monomer units. As a result, as shown in Table 3, it was confirmed that the present PHA is PHA containing 3HBzB as monomer units.

TABLE 3

Production of PHA by *Pseudomonas cichorii* strain YN2

| | |
|---|---|
| Dry weight of Cell | 310 mg/L |
| Dry weight of Polymer | 10 mg/L |
| Monomer Unit Composition (peak area ratio) | |
| 3-hydroxyhexanoic acid | 3% |
| 3-hydroxyoctanoic acid | 26% |
| 3-hydroxydecanoic acid | 32% |
| 3-hydroxydodecanoic acid | 14% |
| 3-hydroxydodecenoic acid | 17% |
| 3-hydroxy-4-benzoylbutyric acid | 8% |

This PHA was analyzed in the following measurement conditions using the NMR spectrometer (FT-NMR: Bruker DPX400).

<Measurement Conditions>

Measuring nuclide: $^1H$

Solvent used: $CDCl_3$ (TMS/$CDCl_3$ sealed with a capillary was used as a reference)

Resonance frequency: $^1H$=400 MHz

The $^1H$-NMR spectrum is shown in FIG. 1.

From the $^1H$-NMR spectrum shown in FIG. 1, it was found that the PHA having monomer units represented by the above-described Chemical Formula [2] was obtained.

Further, the molecular weight of the PHA was evaluated by Gel Permeation Chromatography (GPC; Tosoh HLC-8020, column; Polymer Laboratory PL gel MIXED-C (5 μm), solvent; chloroform, converted into polystyrene), thereby obtaining Mn=18,000 and Mw=42,000.

EXAMPLE 2

*Pseudomonas jessenii* strain P161 was inoculated into 200 mL of the M 9 medium containing 0.5% D-glucose and 0.1% BzBA followed by being cultured with shaking at 30° C. at 125 strokes/min. After 48 hr, the cells were recovered by centrifugal separation, then resuspended into 200 mL of the M 9 medium containing 0.5% D-glucose and 0.1% BzBA without containing a nitrogen source ($NH_4Cl$), followed by being cultured with shaking at 30° C. at 125 strokes/min. After 42 hr, the cells were recovered by centrifugal separation, cleaned once with cold methanol and lyophilized.

This lyophilized pellet was suspended into 20 mL chloroform and stirred at 60° C. for 20 hr, and the PHA was extracted. After filtrating the extracted solution through a membrane filter with the pore size of 0.45 μm, it was concentrated with a rotary evaporator, and the concentrated solution was reprecipitated in cold methanol, further only the precipitate was recovered followed by vacuum drying to obtain PHA.

After performing methanolysis of the obtained PHA according to the conventional method, it was analyzed using a gas chromatography-mass spectrometer (GC-MS, Shimadzu QP-5050, EI method) to identify the methyl ester compound of PHA monomer units. As a result, as shown in Table 4, it was confirmed that the present PHA is PHA containing 3HBzB as monomer units.

TABLE 4

Production of PHA by *Pseudomonas jessenii* strain P161

| | |
|---|---|
| Dry Weight of Cell | 310 mg/L |
| Dry weight of Polymer | 25 mg/L |
| Monomer Unit Composition (peak area ratio) | |
| 3-hydroxyhexanoic acid | 3% |
| 3-hydroxyoctanoic acid | 32% |
| 3-hydroxynonanoic acid | 2% |
| 3-hydroxydecanoic acid | 32% |
| 3-hydroxydodecanoic acid | 7% |
| 3-hydroxydodecenoic acid | 24% |
| 3-hydroxy-4-benzoylbutyric acid | 1% |

EXAMPLE 3

*Pseudomonas cichorii* strain YN2 was inoculated into 200 mL of the M 9 medium containing 0.5% D-glucose and 0.1% BzVA followed by being cultured with shaking at 30° C. at 125 strokes/min. After 48 hr, the cells were recovered by centrifugal separation, then resuspended into 200 mL of the M 9 medium containing 0.5% D-glucose and 0.1% BzVA without containing a nitrogen source ($NH_4Cl$), followed by being cultured with shaking at 30° C. at 125 strokes/min. After 42 hr, the cells were recovered by centrifugal separation, cleaned once with cold methanol and lyophilized.

This lyophilized pellet was suspended into 20 mL chloroform and stirred at 60° C. for 20 hr, and PHA was extracted. After filtrating the extracted solution through a membrane filter with the pore size of 0.45 μm, it was concentrated with a rotary evaporator, and the concentrated solution was reprecipitated in cold methanol, further only the precipitate was recovered followed by vacuum drying to obtain PHA.

After performing methanolysis of the obtained PHA according to the conventional method, it was analyzed using a gas chromatography-mass spectrometer (GC-MS, Shimadzu QP-5050, EI method) to identify the methyl ester compound of PHA monomer units. As a result, as shown in Table 5, it was confirmed that the present PHA is PHA containing 3HBzV as monomer units.

TABLE 5

Production of PHA by *Pseudomonas cichorii* strain YN2

| | |
|---|---|
| Dry weight of Cell | 890 mg/L |
| Dry weight of Polymer | 300 mg/L |
| Monomer Unit Composition (peak area ratio) | |
| 3-hydroxyoctanoic acid | 3% |
| 3-hydroxydecanoic acid | 9% |
| 3-hydroxydodecanoic acid | 3% |
| 3-hydroxydodecenoic acid | 5% |
| 3-hydroxy-5-benzoylvaleric acid | 80% |

This PHA was analyzed in the following measurement conditions using the NMR spectrometer (FT-NMR: Bruker DPX400).

<Measurement Conditions>

Measuring nuclide: $^1H$, $^{13}C$

Solvent used: $CDCl_3$ (TMS/$CDCl_3$ sealed with a capillary was used as a reference)

Resonance frequency: $^1H$=400 MHz, $^{13}C$=100 MHz

Figure 2:
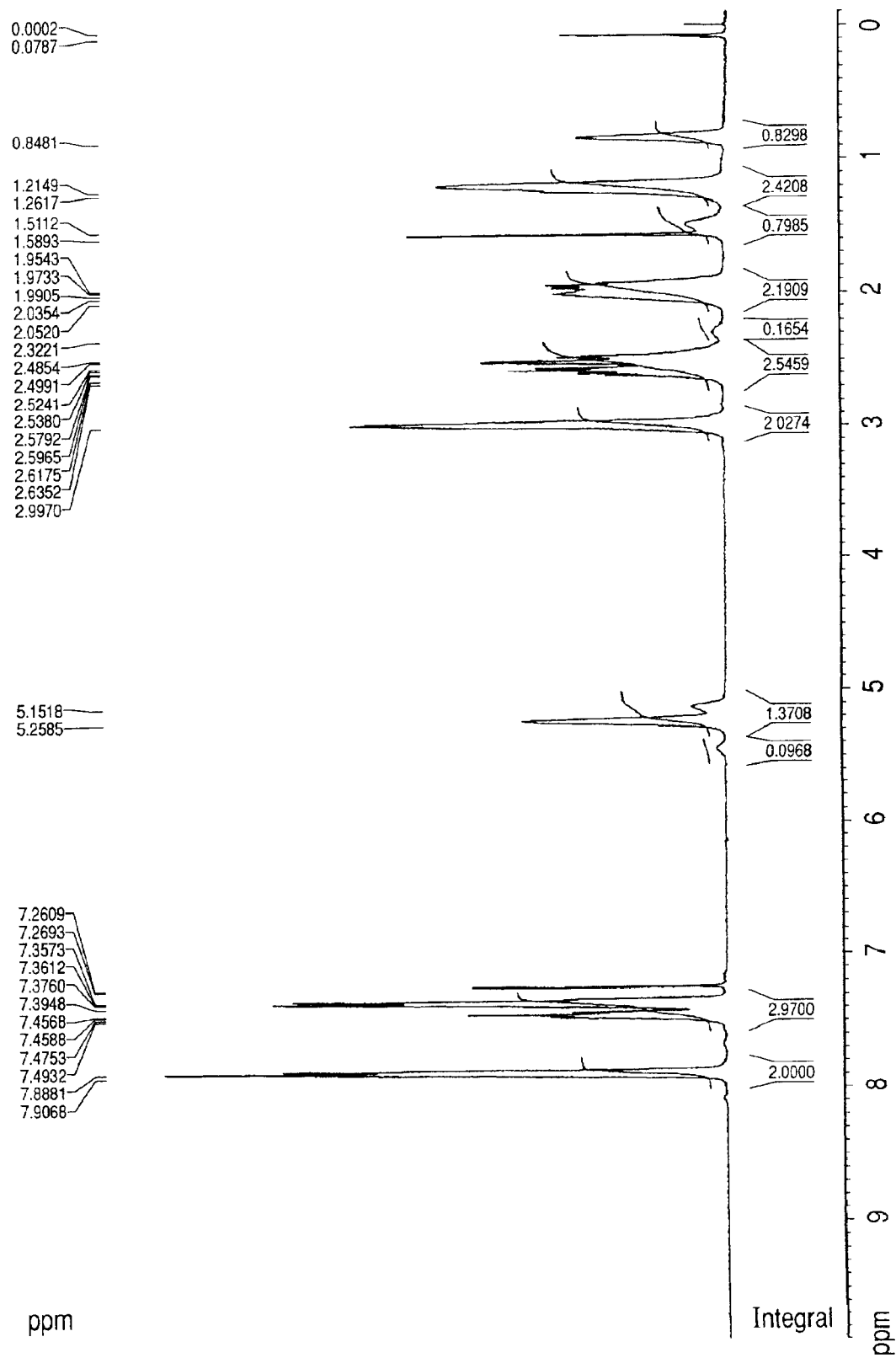
FIG. 2 is a graphical representation showing the $^1$H-NMR spectrum of a polymer using BzVA as a starting material in Example 3.
Figure 3:
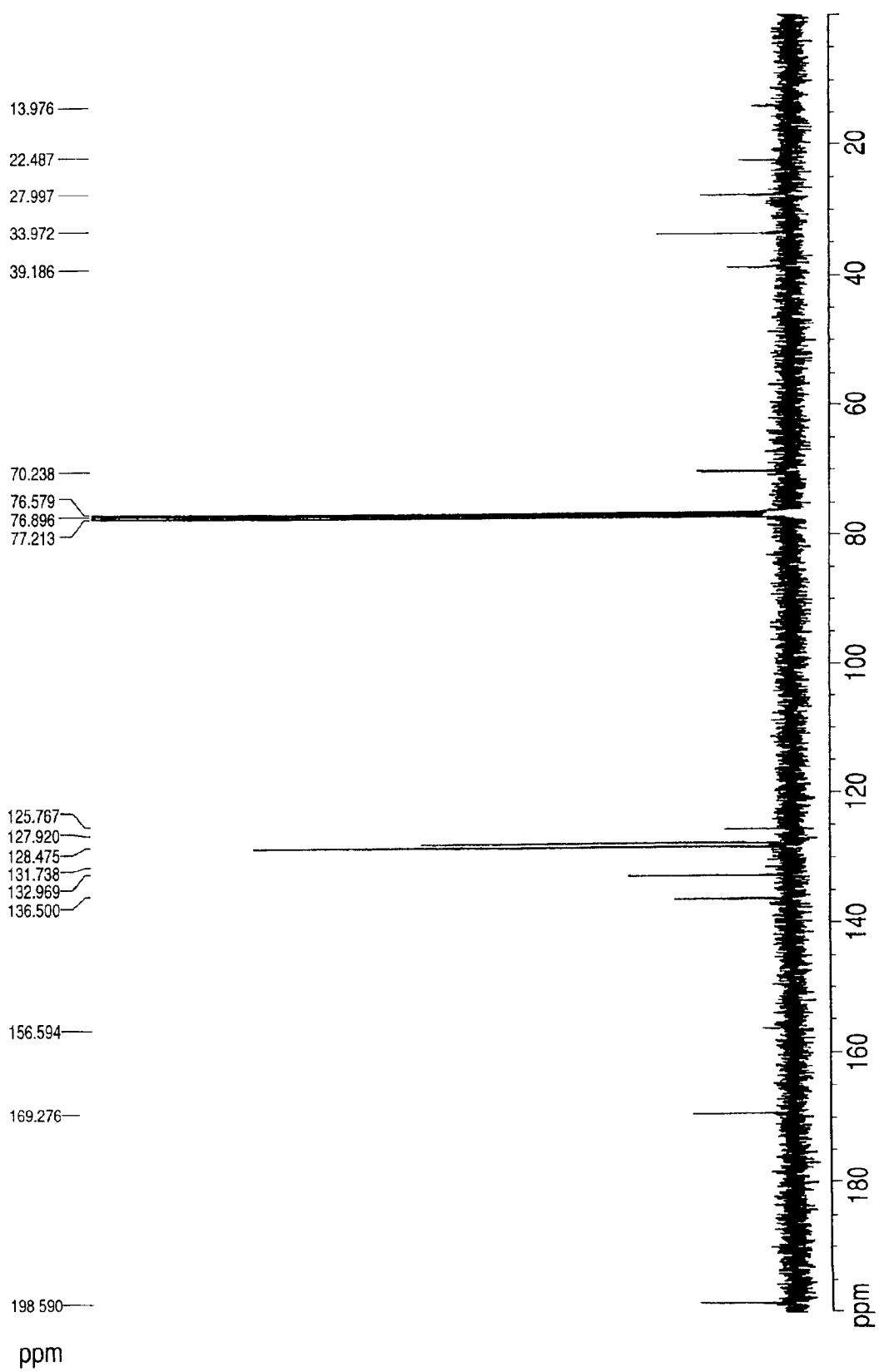
FIG. 3 is a graphical representation showing the $^{13}$C-NMR spectrum of a polymer using BzVA as a starting material in Example 3.

The $^1H$- and $^{13}C$-NMR spectra are shown in FIGS. 2 and 3.

From the $^1$H- and $^{13}$C-NMR spectra shown in FIGS. 2 and 3, it was found that the PHA having monomer units represented by the above-described Chemical Formula [3] was obtained. The assignment results (see Chemical Formula [22]) are shown in Table 6.

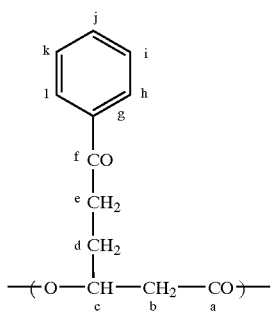

[22]

TABLE 6

Assignment of $^1$H and $^{13}$C-NMR Spectrum

| Location | $^1$H Chemical Shift/ppm | Integral Value | Type | $^{13}$C Chemical Shift/ppm |
|---|---|---|---|---|
| a | — | — | — | 169.3 |
| b | 2.56 | 2 | m | 39.2 |
| c | 5.26 | 1 | m | 70.2 |
| d | 2.04 | 2 | m | 28.0 |
| e | 3 | 2 | m | 34.0 |
| f | — | — | — | 198.6 |
| g | — | — | — | 136.5 |
| h, l | 7.89 | 2 | d | 127.9 |
| i, k | 7.36 | 2 | m | 128.5 |
| j | 7.46 | 1 | t | 133.0 | d: doublet, t: triplet, m: multiplet

Further, the molecular weight of the PHA was evaluated by Gel Permeation Chromatography (GPC; Tosoh HLC-8020, column; Polymer Laboratory PL gel MIXED-C (5 μm), solvent; chloroform, converted into polystyrene), thereby obtaining Mn=330,000 and Mw=1,300,000.

EXAMPLE 4

*Pseudomonas cichorii* strain H45 was inoculated into 200 mL of the M 9 medium containing 0.5% D-glucose and 0.1% BzVA followed by being cultured with shaking at 30° C. at 125 strokes/min. After 48 hr, the cells were recovered by centrifugal separation, then resuspended into 200 mL of the M 9 medium containing 0.5% D-glucose and 0.1% BzVA without containing a nitrogen source (NH$_4$Cl), followed by being cultured with shaking at 30° C. at 125 strokes/min. After 42 hr, the cells were recovered by centrifugal separation, cleaned once with cold methanol and lyophilized.

This lyophilized pellet was suspended into 20 mL chloroform, stirred at 60° C. for 20 hr and the PHA was extracted. After filtrating the extracted solution through a membrane filter with the pore size of 0.45 μm, it was concentrated with a rotary evaporator, and the concentrated solution was reprecipitated in cold methanol, further only the precipitate was recovered followed by vacuum drying to obtain PHA.

After performing methanolysis of the obtained PHA according to the conventional method, it was analyzed using a gas chromatography-mass spectrometer (GC-MS, Shimadzu QP-5050, EI method) to identify the methyl ester compound of PHA monomer units. As a result, as shown in Table 7, it was confirmed that the present PHA is PHA containing 3HBzV as monomer units.

TABLE 7

Production of PHA by *Pseudomonas cichorii* strain H45

| | |
|---|---|
| Dry Weight of Cell | 770 mg/L |
| Dry weight of Polymer | 270 mg/L |
| Monomer Unit Composition (peak area ratio) | |
| 3-hydroxyoctanoic acid | 5% |
| 3-hydroxydecanoic acid | 9% |
| 3-hydroxydodecanoic acid | 3% |
| 3-hydroxydodecenoic acid | 3% |
| 3-hydroxy-5-benzoylvaleric acid | 80% |

EXAMPLE 5

*Pseudomonas jessenii* strain P161 was inoculated into 200 mL of the M 9 medium containing 0.5% D-glucose and 0.1% BzVA followed by being cultured with shaking at 30° C. at 125 strokes/min. After 46 hr, the cells were recovered by centrifugal separation, then resuspended into 200 mL of the M 9 medium containing 0.5% D-glucose and 0.1% BzVA without containing a nitrogen source (NH$_4$Cl), followed by being cultured with shaking at 30° C. at 125 strokes/min. After 41 hr, the cells were recovered by centrifugal separation, cleaned once with cold methanol and lyophilized.

This lyophilized pellet was suspended into 20 mL chloroform and stirred at 60° C. for 20 hr, and PHA was extracted. After filtrating the extracted solution through a membrane filter with the pore size of 0.45 μm, it was concentrated with a rotary evaporator, and the concentrate was reprecipitated in cold methanol, further only the precipitate was recovered followed by vacuum drying to obtain PHA.

After performing methanolysis of the obtained PHA according to the conventional method, it was analyzed using a gas chromatography-mass spectrometer (GC-MS, Shimadzu QP-5050, EI method) to identify the methyl ester compound of PHA monomer units. As a result, as shown in Table 8, it was confirmed that the present PHA is PHA containing 3HBzV as monomer units.

TABLE 8

Production of PHA by *Pseudomonas jessenii* strain P161

| | |
|---|---|
| Dry Weight of Cell | 980 mg/L |
| Dry weight of Polymer | 420 mg/L |
| Monomer Unit Composition (peak area ratio) | |
| 3-hydroxybutyric acid | 1% |
| 3-hydroxyoctanoic acid | 7% |
| 3-hydroxydecanoic acid | 13% |
| 3-hydroxydodecanoic acid | 3% |
| 3-hydroxydodecenoic acid | 4% |
| 3-hydroxy-5-benzoylvaleric acid | 72% |

EXAMPLE 6

*Pseudomonas cichorii* strain YN2 was inoculated into 200 mL of the M 9 medium containing 0.5% D-glucose and 0.1% BzHxA followed by being cultured with shaking at 30° C. at 125 strokes/min. After 46 hr, the cells were recovered by centrifugal separation, then resuspended into 200 mL of the M 9 medium containing 0.5% D-glucose and 0.1% BzHxA without containing a nitrogen source (NH$_4$Cl), followed by being cultured with shaking at 30° C. at 125 strokes/min. After 47 hr, the cells were recovered by centrifugal separation, cleaned once with cold methanol and vacuum-dried.

This vacuum-dried pellet was suspended into 20 mL chloroform and stirred at 60° C. for 20 hr, and PHA was extracted. After filtrating the extracted solution through a membrane filter with the pore size of 0.45 μm, it was concentrated with a rotary evaporator, and the concentrated solution was reprecipitated in cold methanol, further only the precipitate was recovered followed by vacuum drying to obtain PHA.

The obtained PHA was analyzed in the following measurement conditions using the NMR spectrometer (FT-NMR: Bruker DPX400).

<Measurement Conditions>

Measuring nuclide: $^1$H

Solvent used: CDCl$_3$ (TMS/CDCl$_3$ sealed with a capillary was used as a reference)

Resonance frequency: $^1$H=400 MHz

Figure 4:
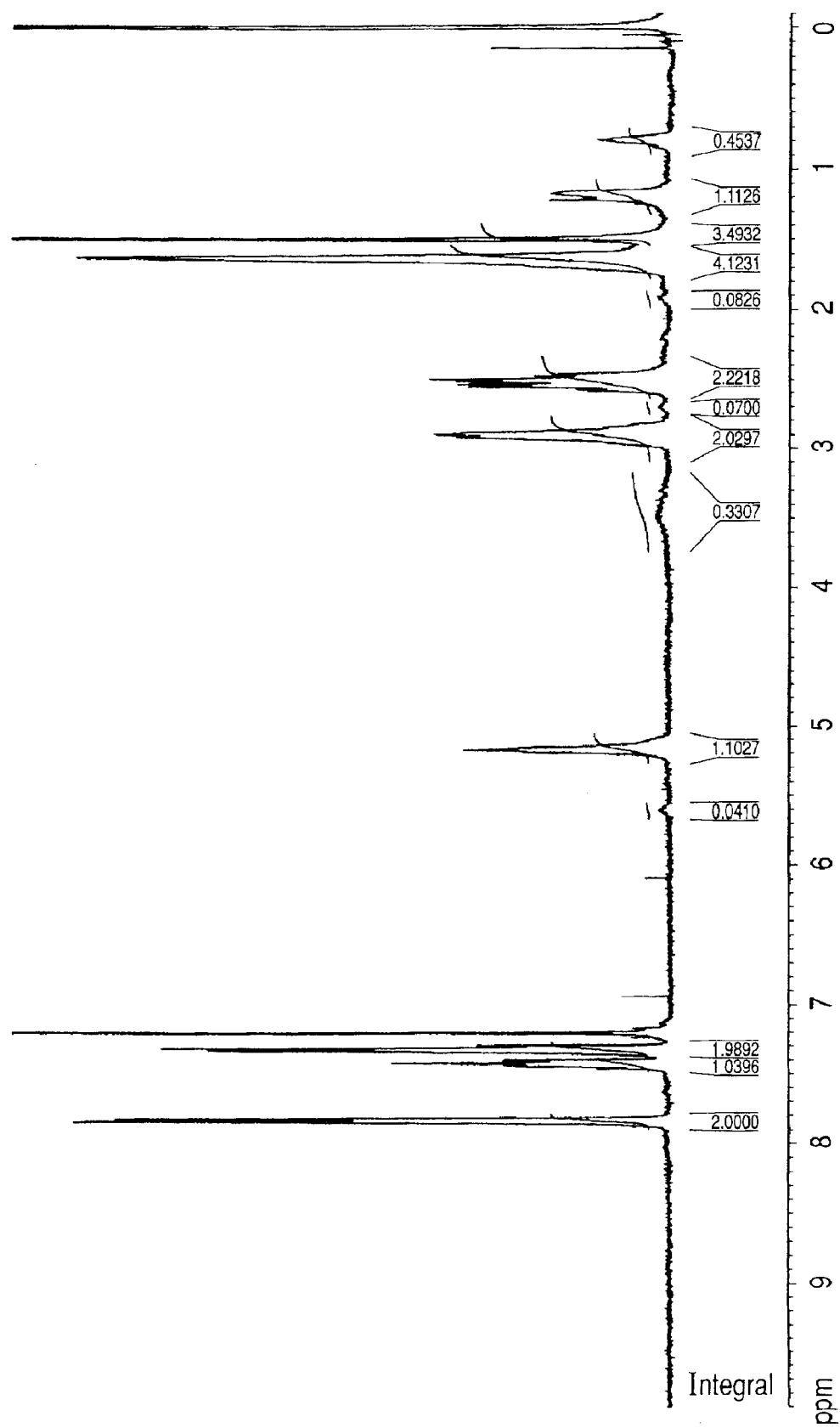
FIG. 4 is a graphical representation showing the $^1$H-NMR spectrum of a polymer using BzHxA as a starting material in Example 1.

The $^1$H-NMR spectra are shown in FIG. 4.

From the $^1$H-NMR spectra shown in FIG. 4, it was found that the PHA having monomer units represented by the above-described Chemical Formula [4] was obtained.

After performing methanolysis of the obtained PHA according to the conventional method, it was analyzed using a gas chromatography-mass spectrometer (GC-MS, Shimadzu QP-5050, EI method) to identify the methyl ester compound of PHA monomer units. The results are shown in Table 9.

TABLE 9

Production of Polyhydroxyalkanoates by Strain YN2

| | |
|---|---|
| Dry Weight of Cell (mg/L) | 710 |
| Weight of Polymer (mg/L) | 180 |
| Monomer Unit Composition (peak area ratio) | |
| 3-hydroxyhexanoic acid | 1.0% |
| 3-hydroxyoctanoic acid | 8.4% |
| 3-hydroxydecanoic acid | 8.9% |
| 3-hydroxydodecanoic acid | 4.4% |
| 3-hydroxydodecenoic acid | 7.2% |
| 3-hydroxytetradecanoic acid | 0.3% |
| 3-hydroxy-6-benzoylhexanoic acid | 69.8% |

From the above results, it was confirmed that the present PHA is PHA containing 3HBzHx as monomer units.

Further, the molecular weight of the PHAs was evaluated by Gel Permeation Chromatography (GPC; Tosoh HLC-8020, column; Polymer Laboratory PL gel MIXED-C (5 μm), solvent; chloroform, converted into polystyrene), thereby obtaining Mn=24,000 and Mw=62,000.

EXAMPLE 7

*Pseudomonas cichorii* strain H45 was inoculated into 200 mL of the M 9 medium containing 0.5% D-glucose and 0.1% BzHxA followed by being cultured with shaking at 30° C. at 125 strokes/min. After 46 hr, the cells were recovered by centrifugal separation, then resuspended into 200 mL of the M 9 medium containing 0.5% D-glucose and 0.1% BzHxA without containing a nitrogen source (NH$_4$Cl), followed by being cultured with shaking at 30° C. at 125 strokes/min. After 47 hr, the cells were recovered by centrifugal separation, cleaned once with cold methanol and vacuum-dried.

This vacuum-dried pellet was suspended into 20 mL chloroform and stirred at 60° C. for 20 hr, and the PHAs were extracted. After filtrating the extracted solution through a membrane filter with the pore size of 0.45 μm, it was concentrated with a rotary evaporator, and the concentrated solution was reprecipitated in cold methanol, further only the precipitate was recovered followed by vacuum drying to obtain PHA.

After performing methanolysis of the obtained PHA according to the conventional method, it was analyzed using a gas chromatography-mass spectrometer (GC-MS, Shimadzu QP-5050, EI method) to identify the methyl ester compound of PHA monomer units. As a result, as shown in Table 10, it was confirmed that the present PHA is PHA containing 3HBzHx as monomer units.

TABLE 10

Production of Polyhydroxyalkanoates by Strain H45

| | |
|---|---|
| Dry Weight of Cell (mg/L) | 760 |
| Weight of Polymer (mg/L) | 140 |
| Monomer Unit Composition (peak area ratio) | |
| 3-hydroxyhexanoic acid | 1.4% |
| 3-hydroxyoctanoic acid | 10.7% |
| 3-hydroxynonanoic acid | 0.1% |
| 3-hydroxydecanoic acid | 8.4% |
| 3-hydroxydodecanoic acid | 2.7% |
| 3-hydroxydodecenoic acid | 3.5% |
| 3-hydroxy-6-benzoylhexanoic acid | 73.2% |

EXAMPLE 8

*Pseudomonas jessenii* strain P161 was inoculated into 200 mL of the M 9 medium containing 0.5% D-glucose and 0.1% BzHxA followed by being cultured with shaking at 30° C. at 125 strokes/min. After 46 hr, the cells were recovered by centrifugal separation, then resuspended into 200 mL of the M 9 medium containing 0.5% D-glucose and 0.1% BzHxA without containing a nitrogen source (NH$_4$Cl), followed by being cultured with shaking at 30° C. at 125 strokes/min. After 47 hr, the cells were recovered by centrifugal separation, cleaned once with cold methanol and lyophilized.

This lyophilized pellet was suspended into 20 mL chloroform and stirred at 60° C. for 20 hr, and PHA was extracted. After filtrating the extracted solution through a membrane filter with the pore size of 0.45 μm, it was concentrated with a rotary evaporator, and the concentrated solution was reprecipitated in cold methanol, further only the precipitate was recovered followed by vacuum drying to obtain PHA.

After performing methanolysis of the obtained PHA according to the conventional method, it was analyzed using a gas chromatography-mass spectrometer (GC-MS, Shimadzu QP-5050, EI method) to identify the methyl ester compound of PHA monomer units. As a result, as shown in Table 11, it was confirmed that the present PHA is PHA containing 3HBzHx as monomer units.

TABLE 11

Production of Polyhydroxyalkanoates by Strain P161

| | |
|---|---|
| Dry Weight of Cell (mg/L) | 540 |
| Weight of Polymer (mg/L) | 200 |
| Monomer Unit Composition (peak area ratio) | |
| 3-hydroxybutyric acid | 0.2% |
| 3-hydroxyhexanoic acid | 2.2% |
| 3-hydroxyoctanoic acid | 21.1% |
| 3-hydroxynonanoic acid | 0.1% |
| 3-hydroxydecanoic acid | 15.9% |
| 3-hydroxydodecanoic acid | 2.9% |
| 3-hydroxydodecenoic acid | 6.0% |
| 3-hydroxytetradecanoic acid | 0.7% |
| 3-hydroxy-6-benzoylhexanoic acid | 50.9% |

EXAMPLE 9

*Pseudomonas cichorii* strain YN2 was inoculated into 200 mL of the M 9 medium containing 0.5% D-glucose and 0.1% BzHpA followed by being cultured with shaking at 30° C. at 125 strokes/min. After 47 hr, the cells were recovered by centrifugal separation, then resuspended into 200 mL of the M 9 medium containing 0.5% D-glucose and 0.1% BzHpA without containing a nitrogen source ($NH_4Cl$), followed by being cultured with shaking at 30° C. at 125 strokes/min. After 43 hr, the cells were recovered by centrifugal separation, cleaned once with cold methanol and vacuum-dried.

This vacuum-dried pellet was suspended into 20 mL chloroform and stirred at 60° C. for 20 hr, and PHA was extracted. After filtrating the extracted solution through a membrane filter with the pore size of 0.45 µm, it was concentrated with a rotary evaporator, and the concentrated solution was reprecipitated in cold methanol, further only the precipitate was recovered followed by vacuum drying to obtain PHA.

The obtained PHA was analyzed in the following measurement conditions using the NMR spectrometer (FT-NMR: Bruker DPX400).

<Measurement Conditions>

Measuring nuclide: $^1H$

Solvent used: $CDCl_3$ ($TMS/CDCl_3$ sealed with a capillary was used as a reference)

Resonance frequency: $^1H$=400 MHz

Figure 5:
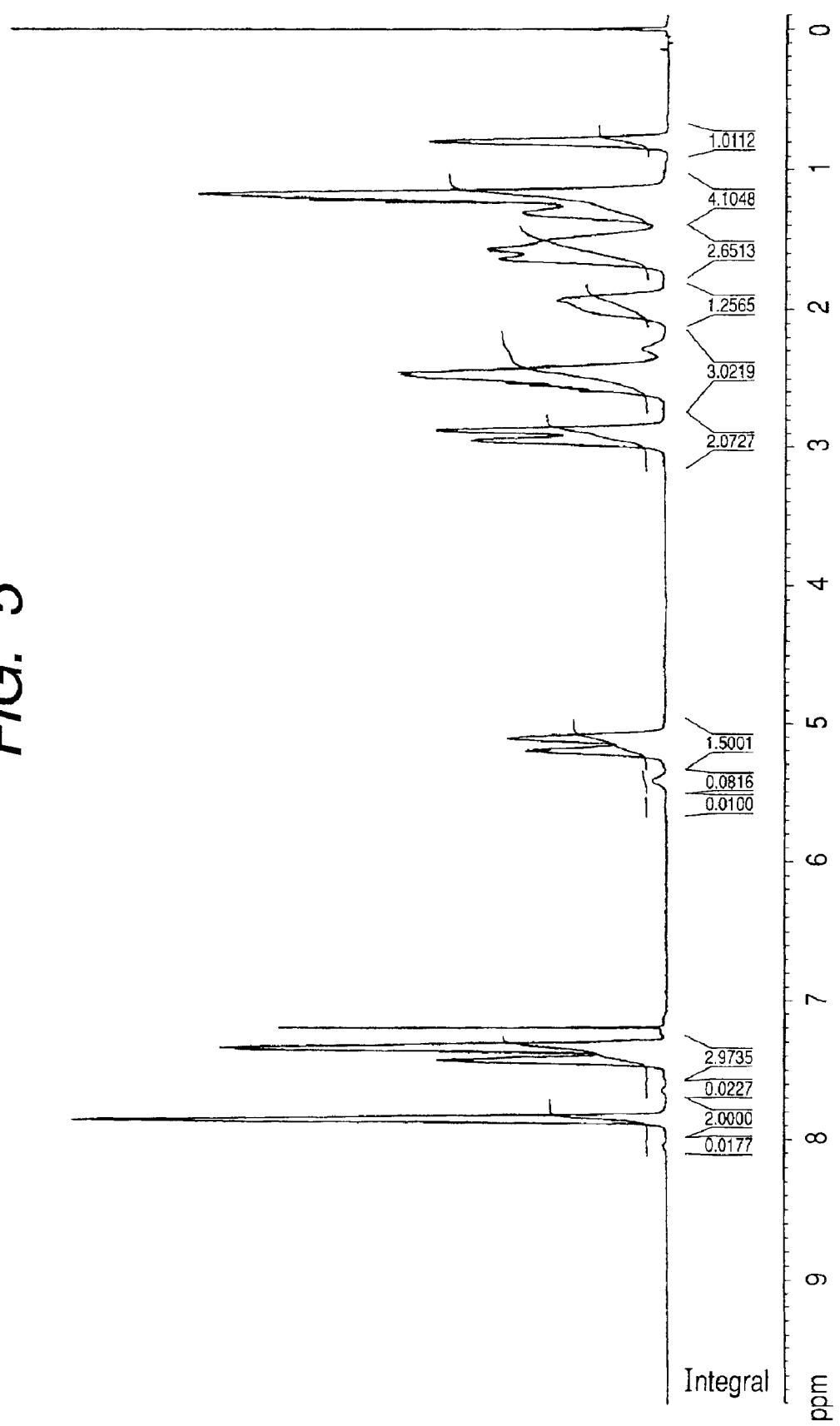
FIG. 5 is a graphical representation showing the $^1$H-NMR spectrum of a polymer using BzHpA as a starting material in Example 9.

The $^1H$-NMR spectra are shown in FIG. 5.

From the $^1H$-NMR spectra shown in FIG. 5, it was found that the PHA having monomer units represented by the above described Chemical Formula [5] was obtained.

After performing methanolysis of the obtained PHA according to the conventional method, it was analyzed using a gas chromatography-mass spectrometer (GC-MS, Shimadzu QP-5050, EI method) to identify the methyl ester compound of PHA monomer units. The results are shown in Table 12.

TABLE 12

Production of Polyhydroxyalkanoates by Strain YN2

| | |
|---|---|
| Dry Weight of Cell (mg/L) | 1440 |
| Weight of Polymer (mg/L) | 590 |
| Monomer Unit Composition (peak area ratio) | |
| 3-hydroxybutyric acid | 0.3% |
| 3-hydroxyhexanoic acid | 0.8% |

TABLE 12-continued

Production of Polyhydroxyalkanoates by Strain YN2

| | |
|---|---|
| 3-hydroxyoctanoic acid | 6.8% |
| 3-hydroxydecanoic acid | 14.3% |
| 3-hydroxydodecanoic acid | 4.6% |
| 3-hydroxydodecenoic acid | 8.2% |
| 3-hydroxy-5-benzoylvaleric acid | 30.8% |
| 3-hydroxy-7-benzoylheptanoic acid | 34.2% |

From the above results, it was confirmed that the present PHA is PHA containing 3HBzHp as monomer units.

Further, the molecular weight of the PHAs was evaluated by Gel Permeation Chromatography (GPC; Tosoh HLC-8020, column; Polymer Laboratory PL gel MIXED-C (5 µm), solvent; chloroform, converted into polystyrene), thereby obtaining Mn=23,000 and Mw=53,000.

EXAMPLE 10

*Pseudomonas cichorii* strain H45 was inoculated into 200 mL of the M 9 medium containing 0.5% D-glucose and 0.1% BzHpA followed by being cultured with shaking at 30° C. at 125 strokes/min. After 47 hr, the cells were recovered by centrifugal separation, then resuspended into 200 mL of the M 9 medium containing 0.5% D-glucose and 0.1% BzHpA without containing a nitrogen source ($NH_4Cl$), followed by being cultured with shaking at 30° C. at 125 strokes/min. After 43 hr, the cells were recovered by centrifugal separation, cleaned once with cold methanol and vacuum-dried.

This vacuum-dried pellet was suspended into 20 mL chloroform and stirred at 60° C. for 20 hr, and PHA was extracted. After filtrating the extracted solution through a membrane filter with the pore size of 0.45 µm, it was concentrated with a rotary evaporator, and the concentrated solution was reprecipitated in cold methanol, further only the precipitate was recovered followed by vacuum drying to obtain PHA.

After performing methanolysis of the obtained PHA according to the conventional method, it was analyzed using a gas chromatography-mass spectrometer (GC-MS, Shimadzu QP-5050, EI method) to identify the methyl ester compound of PHA monomer units. As a result, as shown in Table 13, it was confirmed that the present PHA is PHA containing 3HBzHp as monomer units.

TABLE 13

Production of Polyhydroxyalkanoates by Strain H45

| | |
|---|---|
| Dry Weight of Cell (mg/L) | 830 |
| Weight of Polymer (mg/L) | 160 |
| Monomer Unit Composition (peak area ratio) | |
| 3-hydroxyhexanoic acid | 0.6% |
| 3-hydroxyoctanoic acid | 6.2% |
| 3-hydroxynonanoic acid | 0.1% |
| 3-hydroxydecanoic acid | 6.1% |
| 3-hydroxydodecanoic acid | 1.4% |
| 3-hydroxydodecenoic acid | 1.7% |
| 3-hydroxy-5-benzoylvaleric acid | 38.9% |
| 3-hydroxy-7-benzoylheptanoic acid | 45.0% |

EXAMPLE 11

*Pseudomonas jessenii* strain P161 was inoculated into 200 mL of the M 9 medium containing 0.5% D-glucose and 0.1% BzHpA followed by being cultured with shaking at 30°

C. at 125 strokes/min. After 47 hr, the cells were recovered by centrifugal separation, then resuspended into 200 mL of the M 9 medium containing 0.5% D-glucose and 0.1% BzHpA without containing a nitrogen source (NH$_4$Cl), followed by being cultured with shaking at 30° C. at 125 strokes/min. After 43 hr, the cells were recovered by centrifugal separation, cleaned once with cold methanol and lyophilized.

This lyophilized pellet was suspended into 20 mL chloroform and stirred at 60° C. for 20 hr, and PHA was extracted. After filtrating the extracted solution through a membrane filter with the pore size of 0.45 μm, it was concentrated with a rotary evaporator, and the concentrated solution was reprecipitated in cold methanol, further only the precipitate was recovered followed by vacuum drying to obtain PHA.

After performing methanolysis of the obtained PHA according to the conventional method, it was analyzed using a gas chromatography-mass spectrometer (GC-MS, Shimadzu QP-5050, EI method) to identify the methyl ester compound of PHA monomer units. As a result, as shown in Table 14, it was confirmed that the present PHA is PHA containing 3HBzHp as monomer units.

TABLE 14

Production of Polyhydroxyalkanoates by Strain P161

| | |
|---|---|
| Dry Weight of Cell (mg/L) | 1000 |
| Weight of Polymer (mg/L) | 420 |
| Monomer Unit Composition (peak area ratio) | |
| 3-hydroxybutyric acid | 0.2% |
| 3-hydroxyhexanoic acid | 0.9% |
| 3-hydroxyoctanoic acid | 9.0% |
| 3-hydroxydecanoic acid | 13.7% |
| 3-hydroxydodecanoic acid | 3.2% |
| 3-hydroxydodecenoic acid | 5.0% |
| 3-hydroxy-5-benzoylvaleric acid | 29.4% |
| 3-hydroxy-7-benzoylheptanoic acid | 38.6% |

EXAMPLE 12

*Pseudomonas cichorii* strain YN2 was inoculated into 200 mL of the M 9 medium containing 0.5% D-glucose and 0.1% BzOA followed by being cultured with shaking at 30° C. at 125 strokes/min. After 47 hr, the cells were recovered by centrifugal separation, then resuspended into 200 mL of the M 9 medium containing 0.5% D-glucose and 0.1% BzOA without containing a nitrogen source (NH$_4$Cl), followed by being cultured with shaking at 30° C. at 125 strokes/min. After 43 hr, the cells were recovered by centrifugal separation, cleaned once with cold methanol and vacuum-dried.

This vacuum-dried pellet was suspended into 20 mL chloroform and stirred at 60° C. for 20 hr, and PHA was extracted. After filtrating the extract solution through a membrane filter with the pore size of 0.45 μm, it was concentrated with a rotary evaporator, and the concentrated solution was reprecipitated in cold methanol, further only the precipitate was recovered followed by vacuum drying to obtain PHA.

The obtained PHA was analyzed in the following measurement conditions using the NMR spectrometer (FT-NMR: Bruker DPX400).
<Measurement Conditions>
  Measuring nuclide: $^1$H
  Solvent used: CDCl$_3$
  (TMS/CDCl$_3$ sealed with a capillary was used as a reference)
  Resonance frequency: $^1$H=400 MHz The $^1$H-NMR spectra are shown in FIG. 6.

Figure 6:
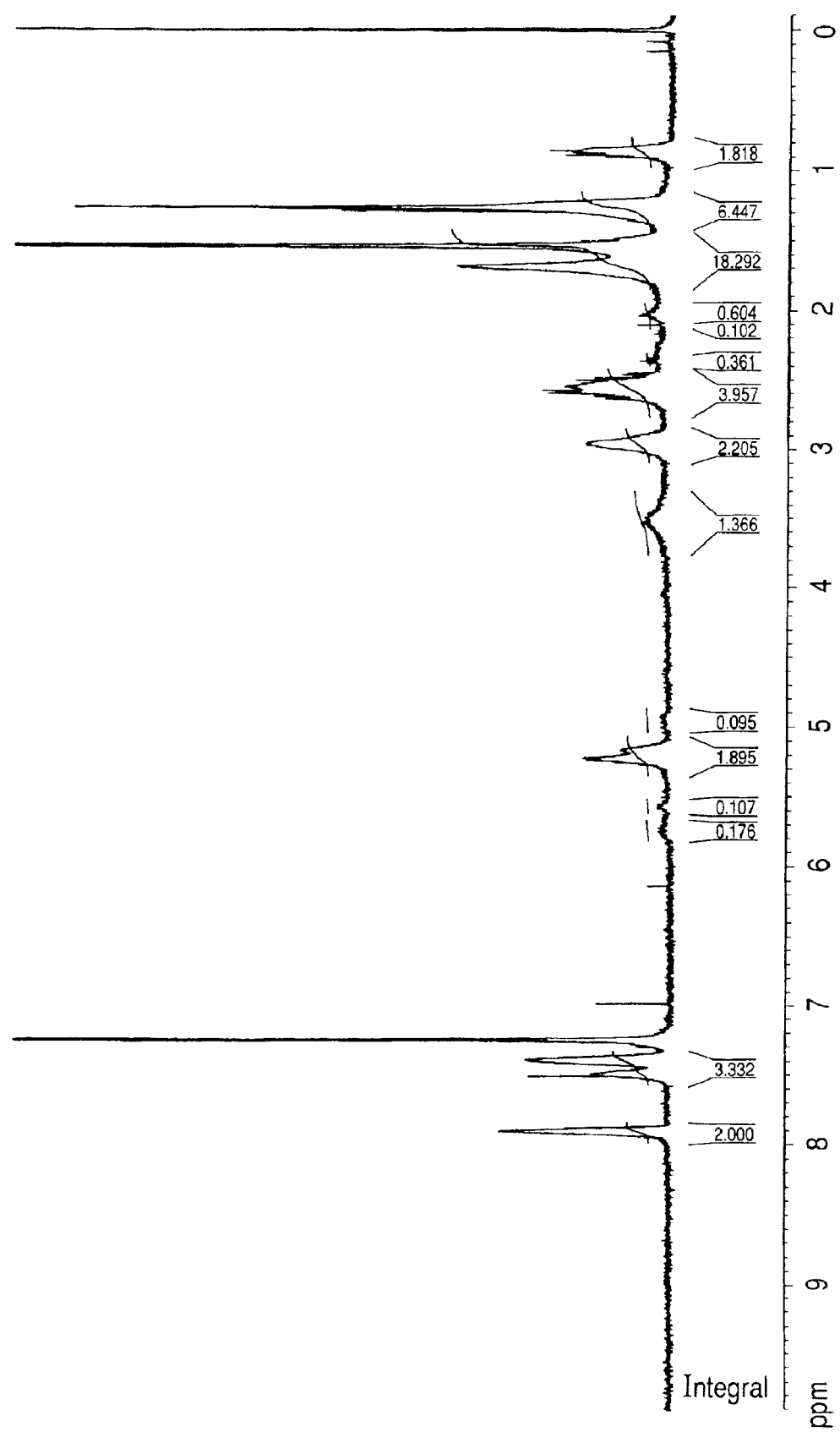
FIG. 6 is a graphical representation showing the $^1$H-NMR spectrum of a polymer using BzOA as a starting material in Example 12.

From the $^1$H-NMR spectra shown in FIG. 6, it was found that the PHA having monomer units represented by the above-described Chemical Formula [6] was obtained.

After performing methanolysis of the obtained PHA according to the conventional method, it was analyzed using a gas chromatography-mass spectrometer (GC-MS, Shimadzu QP-5050, EI method) to identify the methyl ester compound of PHA monomer units. The results are shown in Table 15.

TABLE 15

Production of Polyhydroxyalkanoates by Strain YN2

| | |
|---|---|
| Dry Weight of Cell (mg/L) | 710 |
| Weight of Polymer (mg/L) | 170 |
| Monomer Unit Composition (peak area ratio) | |
| 3-hydroxybutyric acid | 0.1% |
| 3-hydroxyhexanoic acid | 0.4% |
| 3-hydroxyoctanoic acid | 3.9% |
| 3-hydroxynonanoic acid | 0.1% |
| 3-hydroxydecanoic acid | 3.6% |
| 3-hydroxydodecanoic acid | 1.6% |
| 3-hydroxydodecenoic acid | 3.1% |
| 3-hydroxytetradecanoic acid | 0.2% |
| 3-hydroxy-5-phenylvaleric acid | 0.2% |
| 3-hydroxy-6-benzoylhexanoic acid | 37.8% |
| 3-hydroxy-8-benzoyloctanoic acid | 49.0% |

From the above results, it was confirmed that the present PHA is PHA containing 3HBzO as monomer units.

The molecular weight of the PHA was evaluated by Gel Permeation Chromatography (GPC; Tosoh HLC-8020, column; Polymer Laboratory PL gel MIXED-C (5 μm), solvent; chloroform, converted into polystyrene), thereby obtaining Mn=41,000 and Mw=93,000.

EXAMPLE 13

*Pseudomonas cichorii* strain H45 was inoculated into 200 mL of the M 9 medium containing 0.5% D-glucose and 0.1% BzOA followed by being cultured with shaking at 30° C. at 125 strokes/min. After 47 hr, the cells were recovered by centrifugal separation, then resuspended into 200 mL of the M 9 medium containing 0.5% D-glucose and 0.1% BzOA without containing a nitrogen source (NH$_4$Cl), followed by being cultured with shaking at 30° C. at 125 strokes/min. After 43 hr, the cells were recovered by centrifugal separation, cleaned once with cold methanol and vacuum-dried.

This vacuum-dried pellet was suspended into 20 mL chloroform and stirred at 60° C. for 20 hr, and PHA was extracted. After filtrating the extracted solution through a membrane filter with the pore size of 0.45 μm, it was concentrated with a rotary evaporator, and the concentrated solution was reprecipitated in cold methanol, further only the precipitate was recovered followed by vacuum drying to obtain PHA.

After performing methanolysis of the obtained PHA according to the conventional method, it was analyzed using a gas chromatography-mass spectrometer (GC-MS, Shimadzu QP-5050, EI method) to identify the methyl ester compound of PHA monomer units. As a result, as shown in Table 16, it was confirmed that the present PHA is PHA containing 3HBzO as monomer units.

TABLE 16

Production of Polyhydroxyalkanoates by Strain H45

| | |
|---|---|
| Dry Weight of Cell (mg/L) | 720 |
| Weight of Polymer (mg/L) | 160 |
| Monomer Unit Composition (peak area ratio) | |
| 3-hydroxyhexanoic acid | 0.6% |
| 3-hydroxyoctanoic acid | 4.9% |
| 3-hydroxydecanoic acid | 3.3% |
| 3-hydroxydodecanoic acid | 1.9% |
| 3-hydroxydodecenoic acid | 1.1% |
| 3-hydroxy-6-benzoylhexanoic acid | 21.3% |
| 3-hydroxy-8-benzoyloctanoic acid | 66.9% |

EXAMPLE 14

*Pseudomonas jessenii* strain P161 was inoculated into 200 mL of the M 9 medium containing 0.5% D-glucose and 0.1% BzOA followed by being cultured with shaking at 30° C. at 125 strokes/min. After 47 hr, the cells were recovered by centrifugal separation, then resuspended into 200 mL of the M 9 medium containing 0.5% D-glucose and 0.1% BzOA without containing a nitrogen source ($NH_4Cl$), followed by being cultured with shaking at 30° C. at 125 strokes/min. After 43 hr, the cells were recovered by centrifugal separation, cleaned once with cold methanol and lyophilized.

This lyophilized pellet was suspended into 20 mL chloroform and stirred at 60° C. for 20 hr, and PHA was extracted. After filtrating the extract solution through a membrane filter with the pore size of 0.45 µm, it was concentrated with a rotary evaporator, and the concentrated solution was reprecipitated in cold methanol, further only the precipitate was recovered followed by vacuum drying to obtain PHA.

After performing methanolysis of the obtained PHA according to the conventional method, it was analyzed using a gas chromatography-mass spectrometer (GC-MS, Shimadzu QP-5050, EI method) to identify the methyl ester compound of PHA monomer units. As a result, as shown in Table 17, it was confirmed that the present PHA is PHA containing 3HBzO as monomer units.

TABLE 17

Production of Polyhydroxyalkanoates by Strain P161

| | |
|---|---|
| Dry Weight of Cell (mg/L) | 820 |
| Weight of Polymer (mg/L) | 140 |
| Monomer Unit Composition (peak area ratio) | |
| 3-hydroxybutyric acid | 0.9% |
| 3-hydroxyhexanoic acid | 1.4% |
| 3-hydroxyoctanoic acid | 11.5% |
| 3-hydroxynonanoic acid | 0.1% |
| 3-hydroxydecanoic acid | 8.9% |
| 3-hydroxydodecanoic acid | 1.8% |
| 3-hydroxydodecenoic acid | 3.3% |
| 3-hydroxytetradecanoic acid | 0.3% |
| 3-hydroxy-6-benzoylhexanoic acid | 23.1% |
| 3-hydroxy-8-benzoyloctanoic acid | 48.7% |

What is claimed is:

1. A polyhydroxyalkanoate having a monomer unit composition represented by the following Formula [1]:

  [1]

wherein A is at least one monomer unit represented by the following Chemical Formula [2]:

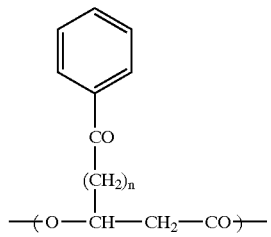  [2]

where n is an integer of 1 to 8; and
B is at least one selected from monomer units represented by the following Chemical Formula [3]:

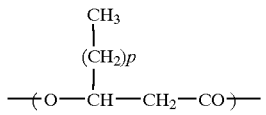  [3]

where p is an integer of 0 to 10, and monomer units represented by the following Chemical Formula [4]:

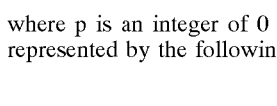  [4]

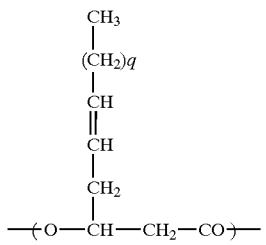

where q is 3 or 5; and
x is not less than 0.01 and less than 1.

2. The polyhydroxyalkanoate according to claim 1, wherein the one or more monomer units include a monomer unit represented by the Chemical Formula [5]:

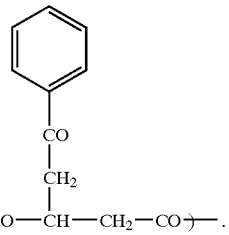  [5]

3. The polyhydroxyalkanoate according to claim 1, wherein the one or more monomer units include a monomer unit represented by the Chemical Formula [6]:

[6]

4. The polyhydroxyalkanoate according to claim 1, wherein the one or more monomer units include a monomer unit represented by the Chemical Formula [7]:

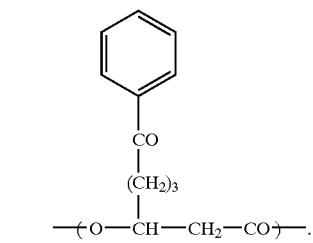  [7]

5. The polyhydroxyalkanoate according to claim 1, wherein the one or more monomer units include a monomer unit represented by the Chemical Formula [8]:

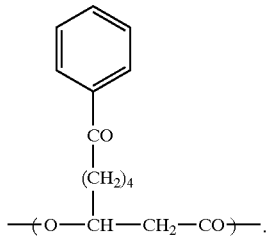

[8]

6. The polyhydroxyalkanoate according to claim 1, wherein the one or more monomer units include a monomer unit represented by the Chemical Formula [9]:

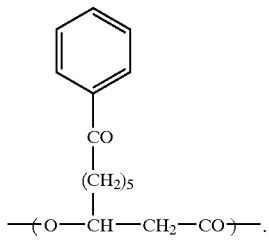

[9]

7. The polyhydroxyalkanoate according to claim 1, wherein the monomer units include a monomer unit represented by the Chemical Formula [6]:

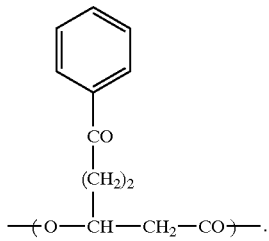

[6]

and a monomer unit represented by the Chemical Formula [8]:

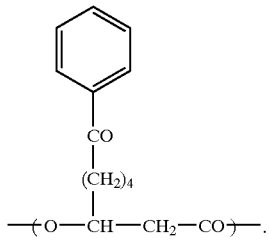

[8]

8. The polyhydroxyalkanoate according to claim 1, wherein the monomer units include a monomer unit represented by the Chemical Formula [7]:

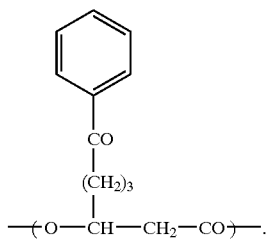

[7]

and a monomer unit represented by the Chemical Formula [9]:

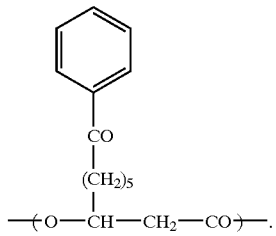

[9]

9. The polyhydroxyalkanoate according to claim 1, wherein the polyhydroxyalkanoate has a number-average molecular weight of 10,000 to 1,000,000.

10. A method for producing a polyhydroxyalkanoate, comprising the step of culturing, in a medium containing a benzoylalkanoic acid, a microorganism capable of synthesizing a polyhydroxyalkanoate having a monomer unit composition represented by the following Formula [1]:

$$A_x B_{(1-x)}$$ [1]

from the benzoylalkanoic acid by utilizing the benzoylalkanoic acid, wherein A is at least one monomer unit represented by the following Chemical Formula [2]:

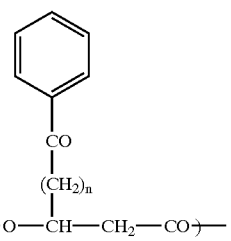

[2]

where n is any integer of 1 to 8;

B is at least one selected from monomer units represented by the following Chemical Formula [3]:

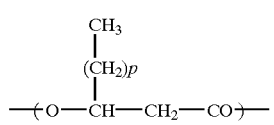

[3]

where p is any integer of 0 to 10, and monomer units represented by the following Chemical Formula [4]:

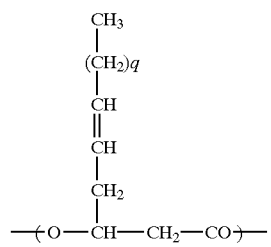

[4]

where q is 3 or 5; and
x is not less than 0.01 to less than 1.

11. The method according to claim 10, wherein the beazoylalkanoic acid is a benzoylalkanoic acid represented by the following Chemical Formula [10]:

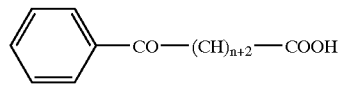

[10]

wherein n is any integer of 1 to 8, and
the polyhydroxyalkanoate is a polyhydroxyalkanoate comprising a monomer unit represented by the following Chemical Formula [11]:

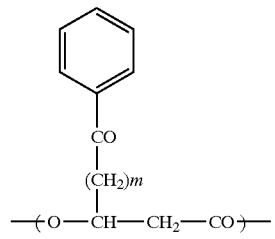

[11]

where m is at least one or more selected from the group consisting of n, n−2, n−4 and n−6, and is an integer not less than 1.

12. The method according to claim 10, wherein the step of culturing the microorganism is a step of culturing the microorganism capable of producing the polyhydroxyalkanoate having the monomer unit composition represented by the Formula [1] in a medium containing the benzoylalkanoic acid and at least one of saccharides, by utilizing the benzoylalkanoic acid.

13. The method according to claim 12, wherein the culture of the microorganism is performed in one step by using a medium containing the benzoylalkanoic acid and the saccharide.

14. The method according to claim 12, wherein the culture of the microorganism is performed in at least two steps by culturing in a medium containing the benzoylalkanoic acid and the saccharide and then culturing in a medium containing the benzoylalkanoic acid and the saccharide in which a nitrogen source is limited.

15. The method according to claim 12, wherein the saccharide is at least one selected from a group consisting of glucose, fructose and mannose.

16. The method according to claim 10, wherein the microogranism is a microorganism belonging to *Pseudomonas* sp.

17. The method according to claim 16, wherein the microorganism is at least one strain selected from a group consisting of *Pseudomonas cichorii* H45, FERM BP-7374; *Pseudomonas cichorii* YN2, FERM BP-7375; and *Pseudomonas jessenii* P161, FERM BP-7376.

18. The method according to claim 10, wherein the step of culturing the microorganism is a step of culturing a microorganism capable of producing a polyhydroxyalkanoate comprising a monomer unit represented by the following Chemical Formula [5]:

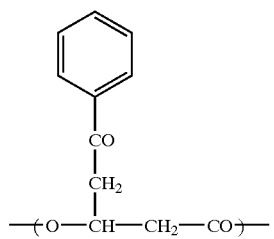

[5]

in a medium containing 4-benzoylbutyric acid represented by the following Chemical Formula [12]:

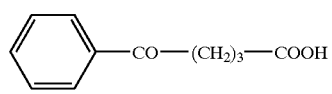

[12]

by utilizing 4-benzoylbutyric acid; and
wherein the produced polyhydroxyalkanoate comprises a monomer unit represented by the Chemical Formula [5].

19. The method according to claim 10, wherein the step of culturing the microorganism is a step of culturing a microorganism capable of producing a polyhydroxyalkanoate comprising a monomer unit represented by the following Chemical Formula [6]:

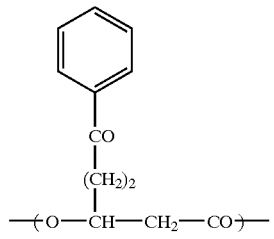

[6]

in a medium containing 5-benzoylvaleric acid represented by the following Chemical Formula [13]:

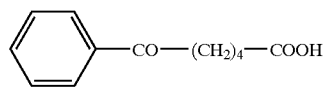

[13]

by utilizing 5-benzoylvaleric acid, and
wherein the produced polyhydroxyalkanoate comprises a monomer unit represented by the Chemical Formula [6].

20. The method according to claim 10, wherein the step of culturing the microorganism is a step of culturing a microorganism capable of producing a polyhydroxyal kanoate comprising a monomer unit represented by the following Chemical Formula [7]:

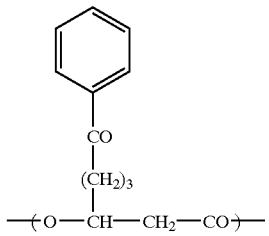
[7]

in a medium containing 6-benzoylhexanoic acid represented by the following Chemical Formula [14]:

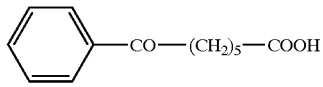
[14]

by utilizing 6-benzoylhexanoic acid, and wherein the produced polyhydroxyalkanoate comprises a monomer unit represented by the Chemical Formula [7].

21. The method according to claim 10, wherein the step of culturing the microorganism is a step of culturing a microorganism capable of producing a polyhydroxyalkanoate comprising a monomer unit represented by the following Chemical Formula [8]:

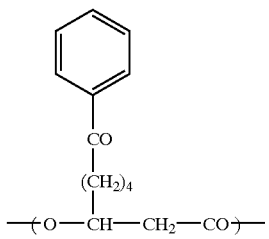
[8]

in a medium containing 7-benzoylheptanoic acid represented by the following Chemical Formula [15]:

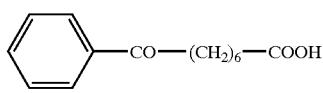
[15]

by utilizing 7-benzoylheptanoic acid, and wherein the produced polyhydroxyalkanoate comprises a monomer unit represented by the Chemical Formula [8].

22. The method according to claim 10, wherein the step of culturing the microorganism is a step of culturing a microorganism capable of producing a polyhydroxyalkanoate comprising a monomer unit represented by the following Chemical Formula [9]:

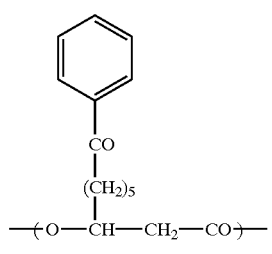
[9]

in a medium containing 8-benzoyloctanoic acid represented by the following Chemical Formula [16]:

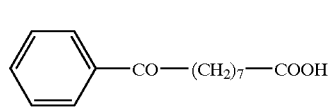
[16]

by utilizing 8-benzoyloctanoic acid, and wherein the produced polyhydroxyalkanoate comprises the monomer unit represented by the following Chemical Formula [9].

23. The method according to claim 10, wherein the step of culturing the microorganism is a step of culturing a microorganism capable of producing a polyhydroxyalkanoate comprising monomer units represented by the following Chemical Formula [6]:

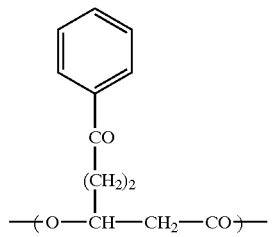
[6]

and the following Chemical Formula [8]:

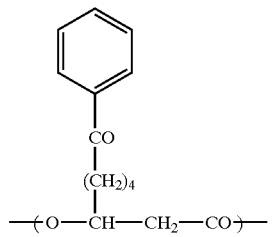
[8]

in a medium containing 7-benzoylheptanoic acid represented by the following Chemical Formula [15]:

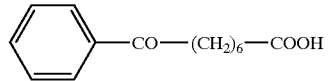

[15]

by utilizing 7-benzoylheptanoic acid, and wherein the produced polyhydroxyalkanoate comprises monomer units represented by the Chemical Formulas [6] and [8].

24. The method according to claim 10, wherein the step of culturing the microorganism is a step of culturing a microorganism capable of producing a polyhydroxyalkanoate comprising monomer units represented by the following Chemical Formula [7]:

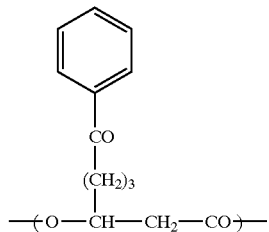

[7]

and the following Chemical Formula [9]:

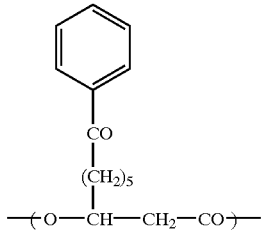

[9]

in a medium containing 8-benzoyloctanoic acid represented by the following Chemical Formula [16]:

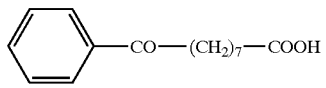

[16]

by utilizing 8-benzoyloctanoic acid, and wherein the produced polyhydroxyalkanoate comprises monomer units represented by the Chemical Formulas [7] and [9].

* * * * *

UNITED STATES PATENT AND TRADEMARK OFFICE
CERTIFICATE OF CORRECTION

PATENT NO. : 6,861,550 B2
DATED : March 1, 2005
INVENTOR(S) : Tsutomu Honma et al.

It is certified that error appears in the above-identified patent and that said Letters Patent is hereby corrected as shown below:

Title page,
Item [56], References Cited, OTHER PUBLICATIONS,
"Reháková" reference, "1994)" should read -- (1994) --.
"Lytl , t al.; "Filtration Siz s of Human Immunod ficiency Virus Typ 1 and Surrogat Virus s Us d To T st Barri r Mat rials;" Appl. and Envirn. Microb., 58 2, (1992) 747-749." should read
-- Lytle, et al.; "Filtration Sizes of Human Immunodeficiency Virus Type 1 and Surrogate Viruses Used To Test Barrier Materials;" Appl. and Environ. Microb., 58 2, (1992) 747-749. --.
"Kim" reference, (first occurrence), "nad" should read -- and --; "Obtain d" should read -- Obtained --; and "*olevorans*" should read -- *oleovorans* --.
"Kim" reference (second occurrence), "*olevorans*" should read -- *oleovorans* --.
"Andújar" reference, "Cycloh xyl" should read -- Cyclohexyl --.
"Ritt r, t al.; "Poly(3-hydroxy-5-ph noxyp ntanoate-co-3-hydroxy-9-ph noxynonanoate) from *Pseudomonas oleovorans*"; Macromol. Ch m. Phys. 195 (1994) 1665-1672." should read
-- Ritter, et al.; "Poly(3-hydroxy-5-phenoxypentanoate-co-3-hydroxy-9-phenoxynonanoate) from *Pseudomonas oleovorans*"; Macromol. Chem. Phys. 195 (1994) 1665-1672. --.

Column 1,
Line 42, "verying" should read -- varying --.

Column 4,
Line 20, "examples" should read -- example --.

Column 7,
Line 67, "fol" should read -- fol- --.

Column 16,
Line 59, "which are added with" should read -- to which has been added --.

Column 17,
Line 15, "is presumably" should read -- are presumably --.

Column 20,
Line 38, "added with" should read -- with added --; and
Line 62, "fluctose," should read -- fructose, --.

UNITED STATES PATENT AND TRADEMARK OFFICE
CERTIFICATE OF CORRECTION

PATENT NO. : 6,861,550 B2
DATED : March 1, 2005
INVENTOR(S) : Tsutomu Honma et al.

It is certified that error appears in the above-identified patent and that said Letters Patent is hereby corrected as shown below:

Column 21,
Line 9, "fluctose" should read -- fructose --;
Line 31, "contains" should read -- contain --; and
Line 51, "COCl$_2$;" should read -- CoCl$_2$; --.

Column 22,
Line 19, "other" should read -- rather --; and
Line 25, "hypochiorite," should read -- hypochlorite, --.

Column 40,
Line 67, "polyhydroxyal" should read -- polyhydroxyal- --.

Column 41,
Line 66, "polyhydroxyal" should read -- polyhydroxyal- --.

Signed and Sealed this

Sixteenth Day of May, 2006

JON W. DUDAS
*Director of the United States Patent and Trademark Office*